(12) United States Patent
Roberts et al.

(10) Patent No.: US 6,721,663 B1
(45) Date of Patent: Apr. 13, 2004

(54) METHOD FOR MANIPULATING PROTEIN OR DNA SEQUENCE DATA IN ORDER TO GENERATE COMPLEMENTARY PEPTIDE LIGANDS

(75) Inventors: Gareth W. Roberts, Cambridge (GB); Jonathan R. Heal, Highbury (GB)

(73) Assignee: Proteom Limited (GB)

( * ) Notice: Subject to any disclaimer, the term of this patent is extended or adjusted under 35 U.S.C. 154(b) by 0 days.

(21) Appl. No.: 09/571,854

(22) Filed: May 16, 2000

(30) Foreign Application Priority Data

Nov. 19, 1999 (GB) .............................................. 9927485

(51) Int. Cl.[7] .......................... C12Q 1/68; C07H 21/02; C07H 21/04; G01N 33/48
(52) U.S. Cl. ............................ 702/19; 435/6; 536/23.1; 536/24.1
(58) Field of Search .............................. 702/19; 435/6; 536/23.1, 24.1

(56) References Cited

U.S. PATENT DOCUMENTS

| 5,081,584 A | 1/1992 | Omichinski et al. | ........ 364/497 |
|---|---|---|---|
| 5,212,072 A | 5/1993 | Blalock et al. | ............ 435/69.1 |

FOREIGN PATENT DOCUMENTS

| WO | WO 97/48060 | 12/1997 |
|---|---|---|
| WO | WO 98/37242 | 8/1998 |
| WO | WO 99/42621 | 8/1999 |
| WO | WO 99/55911 | 11/1999 |

OTHER PUBLICATIONS

Linde, DM, et al. Analysis of Contact Sites in Protein Complexes Does Not Support the Hypothesis Complemtary Peptides Encoded by DNA Antisense Strands. Molecular Biology 31: 357–361 (1997)).*

Aota et al., Codon usage tabulated from the GenBank Genetic Sequence Data, National Institute of Genetics, Mishima, pp. r315–r403.

Amos Bairoch and Rolf Apweiler, The Swiss–Prot protein sequence data bank and its supplement TrEMBL in 1999, Nucleic Acids Research, vol. 21, No. 1 (1999):49–54.

Baranyi et al., The antisense homology box: A new motif within proteins that encodes biologically active peptides, Nature Medicine, vol. 1, No. 9 (Sep. 1995):894–901.

Baranyi et al., Antisense Homology Boxes in C5a Receptor and C5a Anaphylatoxin, The American Association of Immunologists (1996):4591–4601.

Bíró, J., Comparative Analysis of Specificity in Protein–Protein Interactions, Medical Hypotheses, vol. 7 (1981):981–93.

Blalock, J. Edwin, Genetic origins of protein shape and interaction rules, Nature Medicine, vol. 1, No. 9 (Sep. 1995):876–78.

J. Edwin Blalock and Eric M. Smith, Hydropathic Anti–Complementarity of Amino Acids Based on the Genetic Code, Biochemical and Biophysical Research Communications, vol. 121, No. 1 (1984):203–07.

Bost et al., Similarity between the corticotropin (ACTH) receptor and a peptide encoded by an RNA that is complementary to ACTH mRNA, Proc. Natl. Acad. Sci., vol. 82 (Mar. 1985):1372–75.

Kenneth L. Bost and J. Edwin Blalock, Production of Anti–idotypic Antibodies by Immunization with a Pair of Complementary Peptides, Journal of Molecular Recognition, vol. 1, No. 4 (1989):179–83.

Burley et al., Structural genomics: beyond the Human Genome Project, nature genetics, vol. 23 (Oct. 1999):151–57.

Heinz Kohler and Edwin Blalock, The hydropathic binary code: A tool in genomic research?, Nature Biotechnology, vol. 16 (Jul. 1998):601.

Fassina et al., Recognition Properties of Antisense Peptides of Arg[8]–vasopressin/Bovine Neurophysin II Biosynthetic Precursor Sequences, Biochemistry, vol. 28 (1989):8811–18.

M. Fishman and F. L. Adler, The Role of Macrophage–RNA in the Immune Response, The Public Health Research Institute of the City of New York, Inc., pp. 343–348.

Terry Gaasterland, Structural genomics: Bioinformatics in the driver's seat, Nature Biotechnology, vol. 16 (Jul. 1998):625–27.

(List continued on next page.)

Primary Examiner—John S. Brusca
Assistant Examiner—Shubo "Joc" Zhou
(74) Attorney, Agent, or Firm—Finnegan, Henderson, Farabow, Garrett & Dunner, L.L.P.

(57) ABSTRACT

This method enables computational analysis and manipulation of DNA and protein sequence data such as is found in large public databases. The method allows systematic searches of such data to identify portions of sequences which code for key intermolecular surfaces or regions of specific protein targets. In a first example, two amino acid sequences are input (steps 1, 2) to an iterative procedure (steps 4–6). A frame size is selected in terms of a number of sequence elements. The procedure then compares pairs of frames, one from each sequence, to identify intramolecular and intermolecular regions on the basis of relationships between amino acids according to a predetermined coding scheme. The probability of existence of each region within the coding scheme is then evaluated and those regions for which the probability is greater than a predetermined threshold are discarded. The procedure outputs the remaining regions. In a second example, protein structure data is input to an iterative procedure which evaluates for each frame in the protein structure a complementary relationship score between the amino acids in the frame and each amino acid within a predetermined distance from the frame. The procedure outputs each frame for which the score equals or exceeds a predetermined threshold score.

16 Claims, 14 Drawing Sheets

OTHER PUBLICATIONS

Goldstein, Daniel J., An unacknowledged problem for structural genomics?, Nature Biotechnology, vol. 16 (Aug. 1998):696.

Jack Kyte and Russell F. Doolittle, A simple Method for Displaying the Hydropathic Character of a Protein, J. Mol. Biol., vol. 157 (1982):105–32.

Mekler, L.B., Specific Selective Interaction Between Amino Acid Residues of the Polypeptide Chains, Biofizika, vol. 14, No. 14 (1969):581–84.

Robert S. Root–Bernstein and Daniel D. Holsworth, Antisense Peptides: A Critical Mini–Review, J. theor. Biol., vol. 190 (1998):107–19.

Robert S. Root–Bernstein, Amino Acid Pairing, J. theor. Biol., vol. 94 (1982):885–94.

Clare Sansom, Extending the boundaries of molecular modeling, Nature Biotechnology, vol. 16 (Oct. 1998):917–18.

Shai et al., Antisense Peptide Recognition of Sense Peptides: Sequence Simplification and Evaluation of Forces Underlying the Interaction, Biochemistry, vol. 28 (1989):8804–11.

Tau–Mu Yi and Eric S. Lander, Protein Secondary Structure Prediction Using Nearest–neighbor Methods, J. Mol. Bio., vol. 232 (1993):1117–29.

Takei et al., "Analysis of Sense and Antisense Peptide Relationship in Immunoglobulin IgE," in *Peptide Chemistry* (C. Kitada, ed.), pp. 217–220, 1996.

\* cited by examiner

SEQUENCE LISTING

<160> NUMBER OF SEQ ID NOS: 9

<210> SEQ ID NO 1
<211> LENGTH: 17
<212> TYPE: PRT
<213> ORGANISM: Unknown
<220> FEATURE:
<223> OTHER INFORMATION: Hypothetical sequence

<400> SEQUENCE: 1

Ala Thr Arg Gly Arg Asp Ser Arg Asp Glu Arg Ser Asp Glu Arg Thr
1               5                   10                  15

Asp

<210> SEQ ID NO 2
<211> LENGTH: 20
<212> TYPE: PRT
<213> ORGANISM: Unknown
<220> FEATURE:
<223> OTHER INFORMATION: Hypothetical sequence

<400> SEQUENCE: 2

```
Gly Thr Phe Arg Thr Ser Arg Glu Asp Ser Thr Tyr Ser Gly Asp Thr
1               5                   10                  15

Asp Phe Asp Glu
            20
```

<210> SEQ ID NO 3
<211> LENGTH: 8
<212> TYPE: PRT
<213> ORGANISM: Unknown
<220> FEATURE:
<223> OTHER INFORMATION: Hypothetical sequence

<400> SEQUENCE: 3

```
Ala Asp Thr Arg Gly Ser Arg Asp
1               5
```

<210> SEQ ID NO 4
<211> LENGTH: 5
<212> TYPE: PRT
<213> ORGANISM: Unknown
<220> FEATURE:
<223> OTHER INFORMATION: Hypothetical sequence

<400> SEQUENCE: 4

```
Ala Thr Arg Gly Arg
1               5
```

<210> SEQ ID NO 5
<211> LENGTH: 12
<212> TYPE: DNA
<213> ORGANISM: Unknown
<220> FEATURE:
<223> OTHER INFORMATION: Hypothetical sequence

<400> SEQUENCE: 5
aaatttagca tg                                                          12

<210> SEQ ID NO 6
<211> LENGTH: 12
<212> TYPE: DNA
<213> ORGANISM: Unknown
<220> FEATURE:
<223> OTHER INFORMATION: Hypothetical sequence

<400> SEQUENCE: 6
tttaaagcat gc                                                          12

<210> SEQ ID NO 7
<211> LENGTH: 7
<212> TYPE: PRT
<213> ORGANISM: Homo sapiens

<400> SEQUENCE: 7

```
Gln Gly Glu Glu Ser Asn Asp
1               5
```

<210> SEQ ID NO 8
<211> LENGTH: 7
<212> TYPE: PRT
<213> ORGANISM: Homo sapiens

<400> SEQUENCE: 8

```
Leu Ile Thr Val Leu Asn Ile
1               5
```

-continued

```
<210> SEQ ID NO 9
<211> LENGTH: 7
<212> TYPE: PRT
<213> ORGANISM: Unknown
<220> FEATURE:
<223> OTHER INFORMATION: Hypothetical sequence

<400> SEQUENCE: 9

Leu Thr Ile Leu Ile Asn Val
1               5
```

METHOD FOR MANIPULATING PROTEIN OR DNA SEQUENCE DATA IN ORDER TO GENERATE COMPLEMENTARY PEPTIDE LIGANDS

Specific protein interactions are critical events in most biological processes and a clear idea of the way proteins interact, their three dimensional structure and the types of molecules which might block or enhance interaction are critical aspects of the science of drug discovery in the pharmaceutical industry.

Proteins are made up of strings of amino acids and each amino acid in a string is coded for by a triplet of nucleotides present in DNA sequences (Stryer 1997). The linear sequence of DNA code is read and translated by a cell's synthetic machinery to produce a linear sequence of amino acids which then fold to form a complex three-dimensional protein.

The mechanisms which govern protein folding are multifactorial and the summation of a series of interactions between biophysical phenomena and other protein molecules (Stryer 1997). Virtually all molecules signal by non-covalent attachment to another molecule ("binding"). Despite the conceptual simplicity and tremendous importance of molecular recognition, the forces and energetics that govern it are poorly understood. This is owed to the fact that the two primary binding forces (electrostatics and van der Waals interactions) are weak, and roughly of the same order of magnitude. Moreover, binding at any interface is complicated by the presence of solvent (water), solutes (metal ions and salt molecules), and dynamics within the protein, all of which can inhibit or enhance the binding reaction.

In general it is held that the primary structure of a protein determines its tertiary structure. A large volume of work supports this view and many sources of software are available to the scientists in order to produce models of protein structures (Sansom 1998). In addition, a considerable effort is underway in order to build on this principle and generate a definitive database demonstrating the relationships between primary and tertiary protein structures. This endeavour is likened to the human genome project and is estimated to have a similar cost (Gaasterland 1998).

Despite this assembly of background knowledge it is clear that there are considerable limitations in our abilities to predict protein structures and that these become very apparent when computational methods are applied during drug discovery programs. For many experienced practitioners the use of 'docking' programmes (which seek to examine protein-ligand interactions in detail) are 'disappointing' (Sansom 1998).

Consider this example. A typical growth factor has a molecular weight of 15,000 to 30,000 daltons, whereas a typical small molecule drug has a molecular weight of 300–700. Moreover, X-ray crystal structures of small molecule-protein complexes (such as biotin-avidin) or enzyme-substrates show that they usually bind in crevices, not to flat areas of the protein. Thus relative to enzymes and receptors, protein-protein targets are non-traditional and the pharmaceutical community has had very limited success in developing drugs that bind to them using currently available approaches to lead discovery. High throughput screening technologies in which large (combinatorial) libraries of synthetic compounds are screened against a target protein(s) have failed to produce a significant number of lead compounds.

It is possible that a large portion of the difficulties experienced in attempting to apply such computer programs to drug discovery result from an over-reliance on the consensus dogma that primary structure predicts tertiary structure.

This consensus view of the determinants of protein structure has been re-evaluated in the light of experiments with colicin E1 (Goldstein 1998). This scientific work demonstrated that 'modules of secondary structure that make up a given protein are not rigidly constrained in a single set of interactions that lead to a unique three-dimensional structure' (Goldstein 1998).

The data generated in such studies also presents further issues for large structural projects such as that described by Gaasterland (1998). Proteins are identified and their function ascribed by the homology searches for particular structural elements associated with a given function (e.g. transmembrane domains, enzyme cleavage sites, β-barrel fold etc.). In effect there exists a circular logic to the way in which protein structures are explored and described and this hampers our understanding of the true biological significance since we are only searching for those things we already know.

'Given these considerations, structural genomists might consider assigning a high priority to understanding the extent to which protein-protein and other molecular interactions determine native folding patterns before their databases get too full' (Goldstein 1998).

The binding of large proteinaceous signaling molecules (such as hormones) to cellular receptors regulates a substantial portion of the control of cellular processes and functions. These protein-protein interactions are distinct from the interaction of substrates to enzymes or small molecule ligands to seven-transmembrane receptors. Protein-protein interactions occur over relatively large surface areas, as opposed to the interactions of small molecule ligands with serpentine receptors, or enzymes with their substrates, which usually occur in focused "pockets" or "clefts."

Many major diseases result from the inactivity or hyperactivity of large protein signaling molecules. For example, diabetes mellitus results from the absence or ineffectiveness of insulin, and dwarfism from the lack of growth hormone. Thus, simple replacement therapy with recombinant forms of insulin or growth hormone heralded the beginnings of the biotechnology industry. However, nearly all drugs that target protein-protein interactions or that mimic large protein signaling molecules are also large proteins. Protein drugs are expensive to manufacture, difficult to formulate, and must be given by injection or topical administration.

It is generally believed that because the binding interfaces between proteins are very large, traditional approaches to drug screening or design have not been successful. In fact, for most protein-protein interactions, only small subsets of the overall intermolecular surfaces are important in defining binding affinity.

'One strongly suspects that the many crevices, canyons, depressions and gaps, that punctuate any protein surface are places that interact with numerous micro- and macro-molecular ligands inside the cell or in the extra-cellular spaces, the identity of which is not known' (Goldstein 1998).

Despite these complexities, recent evidence suggests that protein-protein interfaces are tractable targets for drug design when coupled with suitable functional analysis and more robust molecular diversity methods. For example, the interface between hGH and its receptor buries ~1300 Sq. Angstroms of surface area and involves 30 contact side chains across the interface. However, alanine-scanning mutagenesis shows that only eight side-chains at the center of the interface (covering an area of about 350 Sq. Angstroms) are crucial for affinity. Such "hot spots" have been found in numerous other protein-protein complexes by alanine-scanning, and their existence is likely to be a general phenomenon.

The problem therefore is to define the small subset of regions that define the binding or functionality of the protein.

The important commercial reason for this is that a more efficient way of doing this would greatly accelerate the process of drug development.

These complexities are not insoluble problems and newer theoretical methods should not be ignored in the drug design process. Nonetheless, in the near future there are no good algorithms that allow one to predict protein binding affinities quickly, reliably, and with high precision (Sunesis website 17/9/99).

The invention provides a method and a software tool for processing sequence data and a method and a software tool for protein structure analysis, and the data forming the product of each method, as defined in the appended independent claims to which reference should be made. Preferred or advantageous features of the invention are set out in dependent subclaims.

The invention provides a method and a software tool for use in analysing and manipulating sequence data (e.g. both DNA and protein) such as is found in large databases (see Table 1). Advantageously it may enable the conducting of systematic searches to identify the sequences which code for key intermolecular surfaces or "hot spots" on specific protein targets.

This technology may advantageously have significant applications in the application of informatics to sequence databases in order to identify lead molecules for important pharmaceutical targets.

TABLE 1

PROTEIN AND NUCLEOTIDE SEQUENCE DATABASES AMENABLE FOR ANALYSIS USING THE INVENTION THE CONCEPTUAL BASIS FOR THE INVENTION

| Database | Description |
| --- | --- |
| Major Nucleic acid databases | |
| Genbank NCBI National Center for Biotechnology information | The Genbank database is a repository for nucleotide data. The NCBI provides facilities to search for sequences in Genbank by text or by sequence similarity and to submit new sequences. |
| EMBL | The EMBL database is a repository for nucleotide data. The EBI provides facilities to search for sequences by text or by sequence similarity and to submit new sequences. |
| DbEST | The dbEST database is a repository for Expressed Sequence Tags (EST) data. |
| Unigene | The Unigene database is a repository for clustered EST data. UniGene is an experimental system for automatically partitioning EST sequences into a non-redundant set of gene-oriented clusters. Each UniGene cluster contains sequences that represent a unique gene, as well as related information such as the tissue types in which the gene has been expressed and map location. Unigene is split up in sections, catogorized by species origin. The current three sections are Human (hsuinigene), Mouse (mmunigene) and Rat (rnunigene) EST clusters. |

TABLE 1-continued

PROTEIN AND NUCLEOTIDE SEQUENCE DATABASES AMENABLE FOR ANALYSIS USING THE INVENTION THE CONCEPTUAL BASIS FOR THE INVENTION

| Database | Description |
| --- | --- |
| STACK | STACK is a public database of sequences expressed in the human genome. The STACK project aims to make the most comprehensive representation of the sequence of each of the expressed genes in the human genome, by extensive processing of gene fragments to make provide a carefully joined set of consensus sequences for each gene. A new method to extensively process gene fragments to make accurate alignment, prevent errors and provide a carefully joined set of consensus sequences for each gene. |
| Major Protein Sequence databases | |
| SWISS-PROT | Curated protein sequence database which strives to provide a high level of annotations (such as the description of the function of a protein, its domains structure, post-translational modifications, variants, etc), a minimal level of redundancy and high level of integration with other databases. |
| TrEMBL | Supplement of SWISS-PROT that contains all the translations of EMBL nucleotide sequence entries not yet integrated in SWISS-PROT. |
| OWL | Non-redundant composite of 4 publicly available primary sources: SWISS-PROT, PIR (1–3), GenBank (translation) and NRL-3D. SWISS-PROT is the highest priority source, all others being compared against it to eliminate identical and trivially different sequences. The strict redundancy criteria render OWL relatively "small" and hence efficient in similarity searches. |
| PIR Protein Information Resource | A comprehensive, annotated, and non-redundant set of protein sequence databases in which entries are classified into family groups and alignments of each group are available. |
| SPTR | Comprehensive protein sequence database that combines the high quality of annotation in SWISS-PROT with the completeness of the weekly updated translation of protein coding sequences from the EMBL nucleotide database. |
| NRL_3D | The NRL_3D database is produced by PIR from sequence and annotation information extracted from the Brookhaven Protein Databank (PDB) of crystallographic 3D structures. |

The Origins of Complementary Peptide Theory

DNA is composed of two helical strands of nucleotides (see FIG. 10). The concepts governing the genetic code and the fact that DNA codes for protein sequences are well known (Stryer 1997). The 'sense' strand codes for the protein, and as such, attracts all the attention of molecular biologists and protein chemists alike. The purpose of the other 'anti-sense' strand is more elusive. To most, its function is relegated to that of a molecular 'support' for the 'sense' strand, which is used when DNA is replicated (Stryer 1997) but is of little immediate functional significance for the day to day activities of cellular processes.

Some research would suggest a greater role of the anti-sense strand of DNA above that of the basic conceptual model of replication. In particular, it had been noticed that there appeared to be a potential functional relationship between sense and anti-sense strands in viruses. Mekler (1969) observed that several minus stranded virus complexes contained protein components translated from the mRNA complementary to the RNA of the viral gene. Mekler postulated that the significance of this finding was that because this viral protein interacts strongly with the RNA from which the mRNA was generated, a peptide chain may associate specifically with the coding strand of its own gene. It was later thought that this may provide a rationale for the ability of a protein to regulate the transcription of its own gene.

Mekler's original theory was supported by studies on antigen processing pathways. Specifically, an antibody-synthesizing RNA complex was found to bind to its antigen with high affinity (Fishman and Adler, 1967). Mekler contended that these results demonstrated the ability of a protein antigen to regulate its own synthesis by binding to the mRNA encoding the antibody (Mekler, 1969). As the binding between the active centre of the antibody and the antigenic determinant is well known to be based on associations of polypeptide chains, he purported that two inter-acting polypeptides may be encoded in complementary strands of DNA (FIG. 11). Mekler also analysed the proposed interacting regions of pancreatic ribonuclease A and recorded that reading the complementary RNA of one of the interacting chains in the 5'-3' direction yielded the sequence of the other interactant. From these observations he suggested that there existed a specific code of interaction between amino acid side chains encoded by complementary codons at the RNA level (Table 2).

Collectively, these observations represented the first predictions of a sense-complementary peptide-binding complex.

One key feature of Mekler's theory was that due to the degeneracy of the genetic code one amino acid may be complementary related to as many as four others, allowing for a large variety of possible interacting sequences (Table 2).

TABLE 2

THE AMINO ACID PAIRINGS RESULTING FROM READING THE ANTICODON FOR
NATURALLY OCCURING AMINO ACID RESIDUES IN THE 5'-3' DIRECTION

| Amino Acid | codon | Complementary codon | Complementary Amino acid | Amino Acid | codon | Complementary codon | Complementary Amino acid |
|---|---|---|---|---|---|---|---|
| Alanine | GCA | UGC | Cysteine | Serine | UCA | UGA | Stop |
| | GCG | CGC | Arginine | | UCC | GGA | Glycine |
| | GCC | GGC | Glycine | | UCG | CGA | Arginine |
| | GCU | AGC | Serine | | UCU | AGA | Arginine |
| | | | | | AGC | GCU | Alanine |
| | | | | | AGU | ACU | Threonine |
| Arginine | CGG | CCG | Proline | Glutamine | CAA | UUG | Leucine |
| | CGA | UCG | Serine | | CAG | CUG | Leucine |
| | CGC | GCG | Alanine | | | | |
| | CGU | ACG | Threonine | | | | |
| | AGG | CCU | Proline | | | | |
| | AGA | UCU | Serine | | | | |
| Aspartic Acid | GAC | GUC | Valine | Glycine | GGA | UCC | Serine |
| | GAU | AUC | Isoleucine | | GGC | GCC | Alanine |
| | | | | | GGU | ACC | Threonine |
| | | | | | GGG | CCC | Proline |
| Asparagine | AAC | GUU | Valine | Histidine | CAC | GUG | Valine |
| | AAU | AUU | Isoleucine | | CAU | AUG | Methionine |
| Cysteine | UGU | ACA | Threonine | Isoleucine | AUA | UAU | Tyrosine |
| | UGC | GCA | Alanine | | AUC | GAU | Aspartic acid |
| | | | | | AUU | AAU | Asparagine |
| Glutamic Acid | GAA | UUC | Phenylalanine | Leucine | CUG | CAG | Glutamine |
| | GAG | CUC | Leucine | | CUC | GAG | Glutamic acid |
| | | | | | CUU | AAG | Lysine |
| | | | | | UUA | UAA | Stop |
| | | | | | CUA | UAG | Stop |
| | | | | | UUG | CAA | Glutamine |
| | | | | | CUG | CAG | Glutamine |
| Lysine | AAA | UUU | Phenylalanine | Threonine | ACA | UGU | Cysteine |
| | AAG | CUU | Leucine | | ACG | CGU | Arginine |
| | | | | | ACC | GGU | Glycine |
| | | | | | ACU | AGU | Serine |
| Methionine | AUG | CAU | Histidine | Tryptophan | UGG | CCA | Proline |
| Phenylalanine | UUU | AAA | Lysine | Tyrosine | UAC | GUA | Valine |
| | UUC | GAA | Glutamic Acid | | UAU | AUA | Isoleucine |
| Proline | CCA | UGG | Tryptophan | Valine | GUA | UAC | Tyrosine |
| | CCC | GGG | Glycine | | GUG | CAC | Histidine |
| | CCU | AGG | Arginine | | GUC | GAC | Aspartic Acid |
| | CCG | CGG | Arginine | | GUU | AAC | Asparagine |

Further Theoretical Developments

In 1981, Mekler revised his original theory and described a 'general stereochemical genetic code' (Mekler and Idlis, 1981) in which it was reported that the complementary pairings detailed in the above table formed three distinct groupings (FIG. 11).

Mekler noted that, in general, amino acids with non-polar side chains were related by complementary code to amino acids with polar side chains. He did not provide an explanation for this. Further theoretical considerations on the possibility of complementary-sense peptide recognition were independently developed by Biro (1981), Root-Bernstein (1982) and Blalock and Smith (1984). Biro (1981) conducted a computational comparison of DNA sequences: encoding protein ligand-receptor segments and showed that there were many complementary regions between them, giving rise to complementary related polypeptides.

Blalock and Smith (1984) observed that the hydropathic character of an amino acid residue is related to the identity of the middle letter of the triplet codon from which it is transcribed. Specifically, a triplet codon with thymine (T) as its middle base codes for a hydrophobic residue whilst adenine (A) codes for a hydrophilic residue. A triplet codon with middle bases cytosine (C) or guanine (G) encode residues which are relatively neutral and with similar hydropathy scores. Hydropathy is an index of the affinity of an amino acid for a polar environment, hydrophilic residues yielding a more negative score, whilst hydrophobic residues exhibit more positive scores. Kyte and Doolittle (1982) conceived the most widely used scale of this type. The observed relationship between the middle base of a triplet codon and residue hydropathy entails that peptides encoded by complementary DNA will exhibit complementary, or inverted, hydropathic profiles.

It was proposed that because two peptide sequences encoded in complementary DNA strands display inverted hydropathic profiles, they may form amphipathic secondary structures, and bind to one another (Bost et al., 1985).

Complementary peptides have been reported to form binding complexes with their 'sense' peptide counterparts (Root-Bernstein and Holsworthy, 1998). Evidence of such an interaction has now been reported for over forty different systems from many different authors (Table 3).

The reports listed cite experiments showing specific interactions between complementary peptide pairs. As such they demonstrate a variety of ways in which these peptide ligands may be utilised.

The scope of this analysis for explaining the interactions between proteins was further developed by Blalock to propose a Molecular Recognition Theory (MRT) (Bost and Blalock 1985, Blalock 1995, FIG. 13). This theory suggests that a 'molecular recognition' code of interaction exists between peptides encoded by complementary strands of DNA based on the observation that such peptides will exhibit inverted hydropathic profiles.

Blalock suggested that it is the linear pattern of amino acid hydropathy scores in a sequence (rather than the combination of specific residue identities), that defines the secondary structure environment. Furthermore, lie suggested that sequences with inverted hydropathic profiles are complementary in shape by virtue of inverse forces determining their steric relationships.

TABLE 3

LITERATURE REGARDING GENERATION OF
COMPLEMENTARY PEPTIDES WITH BIOLOGICAL EFFECTS

| System tested | Reference Index |
| --- | --- |
| ACTH | Bost et al. (1985) |
| Anaphylatoxin C5a | Baranyi et al. (1996) |

TABLE 3-continued

LITERATURE REGARDING GENERATION OF
COMPLEMENTARY PEPTIDES WITH BIOLOGICAL EFFECTS

| System tested | Reference Index |
| --- | --- |
| Angiogenin | Gho et al. (1997) |
| Angiotensin II | Elton et al. (1988), Soffer et al. (1987) |
| Arginine vasopressin | Johnson et al. (1988), Lu et al. (1991) |
| ☐-endorphin | Shahabi et al. (1992) |
| Big Endothelin | Fassina et al. (1992b) |
| Bradykinin | Fassina et al. (1992c) |
| Calcium mimetic peptide | Dillon et al. (1991) |
| c-Raf protein | Fassina et al. (1989b) |
| Cystatin | Ghiso et al. (1990) |
| Dopamine receptor | Nagy et al (1991) |
| Enkephalin | Carr et al. (1989) |
| Fibrinogen | Pasqualini et al. (1989), Gartner et al. (1991b) |
| Fibronectin | Brentani et al. (1988) |
| ☐-Endorphin | Carr et al. (1986) |
| Gastrin terminal peptide | McGuigan et al. (1992), Jones (1972) |
| GH-RH | Grosvenor and Balint (1989) |
| Idiotypic antibodies | Bost and Blalock (1989) |
| Insulin | Knutson (1988) |
| Integrin | Derrick et al. (1997) |
| Interferon ☐ | Johnson et al. (1982) |
| Interferon ☐ | Scalpol et al. (1992) |
| Interleukin 2 | Weigent et al. (1986), Fassina et al. (1995) |
| Laminin receptor | Castronov, V et al. (1991) |
| LR-RH | Mulchahey et al. (1986) |
| Melanocyte stimulating hormone | Al-Obeidi, F. A. et al. (1989) |
| mosquito oostatic receptor | Borovsky et al. (1994) |
| Myelin protein antibody | Zhou et al. (1993) |
| Nicotinic receptor | Radding et al. (1992) |
| Neurophysin II | Fassina et al (1989b) |
| Ovine prolactin | Bajpai et al. (1991) |
| Opiate receptor | Carr et al. (1987) |
| Prion protein | Martins et al. (1997) |
| Ribonuclease S peptide | Shai et al. (1989) |
| Somatostatin | Campbell-Thompson (1993) |
| Substance P | Bret-Dibat et al. (1994) |
| T15autoreactive antibody | Kang et al. (1988) |
| Vasopressin 1 receptor | Kelly et al. (1990) |
| Vitronectin | Gartner et al. (1991b) |

Deriving a Complementary Peptide in the 3'-5' Reading Frame

As a corollary to his original work, Blalock contended that as well as reading a complementary codon in the usual 5'-3' direction, reading a complementary codon in the 3'-5' would also yield amino acid sequences that displayed opposite hydropathic profiles (Bost et al., 1985). This follows from the observation that the middle base of a triplet codon determines the hydropathy index of the residue it codes for, and thus reading a codon in the reverse direction may change the identity, but not the hydropathic nature of the coded amino acid (Table 4).

Statistical studies at the DNA level must take into account the degeneracy of the genetic code as it allows for the existence of larger inter- or intramolecular complementary sequences without maintaining complementarity at the DNA level. In this vein, recent work by Baranyi et al. (1995) details a new protein structural motif called the Antisense Homology Box (AHB). Following an analysis of a protein sequence data bank for possible intramolecular complementary pairs, it was noted that there are many more regions of complementary peptide complementarity within the structures than statistically expected.

The reported frequency of these motifs is, on average, one per fifty residues. AHB areas have already been shown to be able to act as molecular recognition sites by studies involving function inhibition with peptide complements. Specifically, the endothelin peptide (ET-1) was inhibited by a 14 residue fragment of the endothelin A receptor in a smooth muscle relaxation assay (Baranyi et al., 1996), whilst complementary encoded regions of the C5a receptor antagonize C5a anaphylatoxin (Baranyi et al., 1996). These studies suggest that many interactions in nature may result from contacts between complementary related polypeptides.

complementarity, implying that a peptide's hydropathic character is inextricably linked to the binding mechanism.

This interesting result suggests that binding between two complementary related peptides is determined solely by the hydropathicity. Importantly, it also suggests that the steric nature of the side chain alone does not directly influence the ability of peptides to recognise each other, for in general, residues with similar hydropathic character display a wide distribution of side chain shapes and sizes.

TABLE 4

The relationships between amino acids and the residues encoded in the complementary strand reading 3'-5'

| Amino Acid | Codon | Complementary codon | Complementary Amino acid | Amino Acid | codon | Complementary codon | Complementary Amino acid |
|---|---|---|---|---|---|---|---|
| Alanine | GCA | CGU | Arginine | Serine | UCA | AGU | Serine |
|  | GCG | CGC |  |  | UCC | AGQ | Arginine |
|  | GCC | CGG |  |  | UCG | AGC | Serine |
|  | GCU | CGA |  |  | UCU | AGA | Arginine |
|  |  |  |  |  | AGC | UCG | Serine |
|  |  |  |  |  | AGU | UCA | Serine |
| Arginine | CGG | GCC | Alanine | Glutamine | CAA | GUU | Valine |
|  | CGA | GCU | Alanine |  | CAG | GUC | Valine |
|  | CGC | GCG | Alanine |  |  |  |  |
|  | CGU | GCA | Alanine |  |  |  |  |
|  | AGG | UCC | Serine |  |  |  |  |
|  | AGA | UCU | Serine |  |  |  |  |
| Aspartic Acid | GAC | GUC | Valine | Glycine | GGA | CCU | Proline |
|  | GAU | AUC | Isoleucine |  | GGC | CCG | Proline |
|  |  |  |  |  | GGU | CCA | Proline |
|  |  |  |  |  | GGG | CCC | Proline |
| Asparagine | AAC | UUG | Leucine | Histidine | CAC | GUG | Valine |
|  | AAU | UUA | Leucine |  | CAU | GUA | Valine |
| Cysteine | UGU | ACA | Threonine | Isoleucine | AUA | UAU | Tyrosine |
|  | UGC | ACG | Threonine |  | AUC | UAG | Stop |
|  |  |  |  |  | AUU | UAA | Stop |
| Glutamic Acid | GAA | CUU | Leucine | Leucine | CUG | GAC | Asp |
|  | GAG | CUG | Leucine |  | CUC | GAG | Glutamic acid |
|  |  |  |  |  | CUU | GAA | Glutamic acid |
|  |  |  |  |  | UUA | AAU | Glutamic Acid |
|  |  |  |  |  | CUA | GAU | Glutamic Acid |
|  |  |  |  |  | UUG | AAC | Asparagine |
|  |  |  |  |  | CUG | GAC | Aspartic Acid Asparagine Aspartic Acid |
| Lysine | AAA | UUU | Phenylalanine | Threonine | ACA | UGU | Cysteine |
|  | AAG | UUC | Phenylalanine |  | ACG | UGC | Cysteine |
|  |  |  |  |  | ACC | UGG | Tryptophan |
|  |  |  |  |  | ACU | UGA | Stop |
| Methionine | AUG | UAC | Tyrosine | Tryptophan | UGG | ACC | Threonine |
| Phenylalanine | UUU | AAA | Lysine | Tyrosine | UAC | AUG | Methionine |
|  | UUC | AAG | Lysine |  | UAU | AUA | Isoleucine |
| Proline | CCA | GGU | Glycine | Valine | GUA | CAU | Histidine |
|  | CCC | GGG | Glycine |  | GUG | CAC | Histidine |
|  | CCU | GGA | Glycine |  | GUC | CAG | Glutamine |
|  | CCG | GGC | Glycine |  | GUU | CAA | Glutamine |

A Model of Recognition Based on Hydropathy

Several investigations have been directed at gaining an understanding of how hydropathic profiles and binding constants between complementary peptides are connected. The most comprehensive of these was carried out by Fassina et al. (1989) who studied the relationship between a complementary peptide designed on a computer to maximize complementary hydropathy against a thirteen-residue section of a glycoprotein. The study demonstrates a positive correlation between binding constants, as determined by an affinity binding column assay, and the degree of hydropathic Approaches to Preparing Complementary Peptides The generation of a complementary peptide is straightforward in cases where the DNA sequence information is available. The complementary base sequence is read in either the 5'-3' or 3'-5' direction and translated to the peptide sequence according to the genetic code. In the absence of knowledge of the nucleotide sequence of the sense peptide, many possible permutations of complementary sequences exist, in accordance with the degeneracy of the genetic code (as shown in Tables 2 and 4).

Several approaches to define complementary sequences in such instances have been proposed:

One such approach makes a series of educated guesses based on the use of preferred codon usage tables (Aota et al. 1988) which allows one to assess the probability of a particular codon to be used for each amino acid for a given sequence.

Another approach, where applicable, is to assign the complementary residue to the amino acid which is the most frequent out of all the theoretical complementary residues.

Thus, in a situation where the DNA sequence is unknown, the possible complementary amino acids for a leucine residue are glutamine (3 possible codons), stop (2 possible codons), glutamic acid (1 possible codons) and lysine (1 possible codon). In this case glutamine would be chosen on the basis of statistical weight. Information such as this, along with the use of codon usage tables leads to a consensus approach to limiting the number of possible combinations of complementary sequences. Bost and Blalock (1989), Omichinski et al. (1989) and Shai et al. (1989) have employed methods of this type.

A number of studies have demonstrated the value of this type of approach to designing peptides with real functional utility.

Although some very high affinities have been reported for these peptides ($K_d \sim 10^{-9}$ M), most are of moderate affinity ($K_d \sim 10^{-3} – 10^{-7}$ M). Their potential applications therefore would depend on the affinity attained in a particular system. Lower affinity complementary peptides may be useful for diagnostic tests or for purification of ligands. Higher affinity peptides may serve a purpose in the development of therapeutics, for example a complementary peptide to a coat protein of a virus may interfere with the virus-host interaction at the molecular level, thus providing a strategy to manage this type of disorder.

Although the importance of inverted hydropathy in protein-protein interactions has long been recognized (Blalock and Smith, 1984) there has been little activity to apply this method on a large scale to investigate the complementary peptide partners of many proteins. One such attempt is recorded in the literature. "In the design of computer-based mining tools, no attention has been paid to a unique feature in the genetic code that determines the basic physico-chemical character of the encoded amino acids" (Kohler and Blalock, 1998). They proposed a method to scan DNA sequence banks using the hydropathic binary code, U.S. Pat. No. 5,523,208. The method described differs from the current invention as outlined below.

The current invention finds regions of potentially interacting amino acid sequences by using the relationships outlined in Tables 2 and 4. U.S. Pat. No. 5,523,208 determines regions of potentially interacting peptides by an altogether different method, that of hydropathy scoring. The results of analyses are thus completely different.

The process (algorithms) in by which sequences are analysed are different in the current invention than described U.S. Pat. No. 5,523,208. In particular, the current invention describes different algorithms for the analysis of complementary regions between proteins, or within proteins.

Problems Addressed By the Invention

The current problems associated with design of complementary peptides are:

A lack of understanding of the forces of recognition between complementary peptides An absence of software tools to facilitate searching and selecting complementary peptide pairs from within a protein database.

A lack of understanding of statistical relevance/distribution of naturally encoded complementary peptides and how this corresponds to functional relevance.

Based on these shortfalls, embodiments of the invention describes the following technological advances in this field:

A mini library approach to define forces of recognition between human Interleukin (IL) 1β and its complementary peptides;

A high throughput computer system to analyse an entire database for intra/inter-molecular complementary regions; and A novel (computational) method of analyzing X-ray crystal files for potential discontinuous complementary binding sites.

The Innovation

Studies into preferred complementary peptide pairings between IL-1β and its complementary ligand reveal the importance of both the genetic code and complementary hydropathy for recognition. Specifically, for our example, the genetic code for a region of protein codes for the complementary peptide with the highest affinity. An important observation is that this complementary peptide maps spatially and by residue hydropathic character to the interacting portion of the IL-1R receptor, as elucidated by the X-ray crystal structure Brookhaven reference pdb2itb.ent.

Using these novel observations as guiding principles for analysis, we have developed a computational analysis system to evaluate the statistical and functional relevance of intra/inter- molecular complementary sequences.

This invention provides significant benefits for those interested in:

The analysis and acquisition of peptide sequences to be used in the understanding of protein-protein interactions.

The development of peptides or small molecules which could be used to manipulate these interactions.

The advantages of this invention to previous work in this field include:

Using a valid statistical model. Previously, complementary mappings within protein structures has been statistically validated by assuming that the occurrence of individual amino acids is equally weighted at 1/20 (Baranyi, 1995). Our statistical model takes into account the natural occurrence of amino acids and thus generates probabilities dependent on sequence rather than content per se.

Facilitation of batch searching of an entire database. Previously, investigations into the significance of naturally encoded complementary related sequences have been limited to small sample sizes with non-automated methods. The invention allows for analysis of an entire database at a time, overcoming the sampling problem, and providing for the first time an overview or 'map' of complementary peptide sequences within known protein sequences.

The ability to map complementary sequences as a function of frame size and percentage antisense amino acid content. Previously, no consideration has been given to the significance of the frame length of complementary sequences. Our invention produces a statistical map as

BRIEF DESCRIPTION OF DRAWINGS

The present invention is described with reference to accompanying drawings. In the drawings, like reference numbers indicate identical or functionally similar elements.

FIG. (1) shows a block diagram illustrating one embodiment of a method of the present invention;

Figure 1:
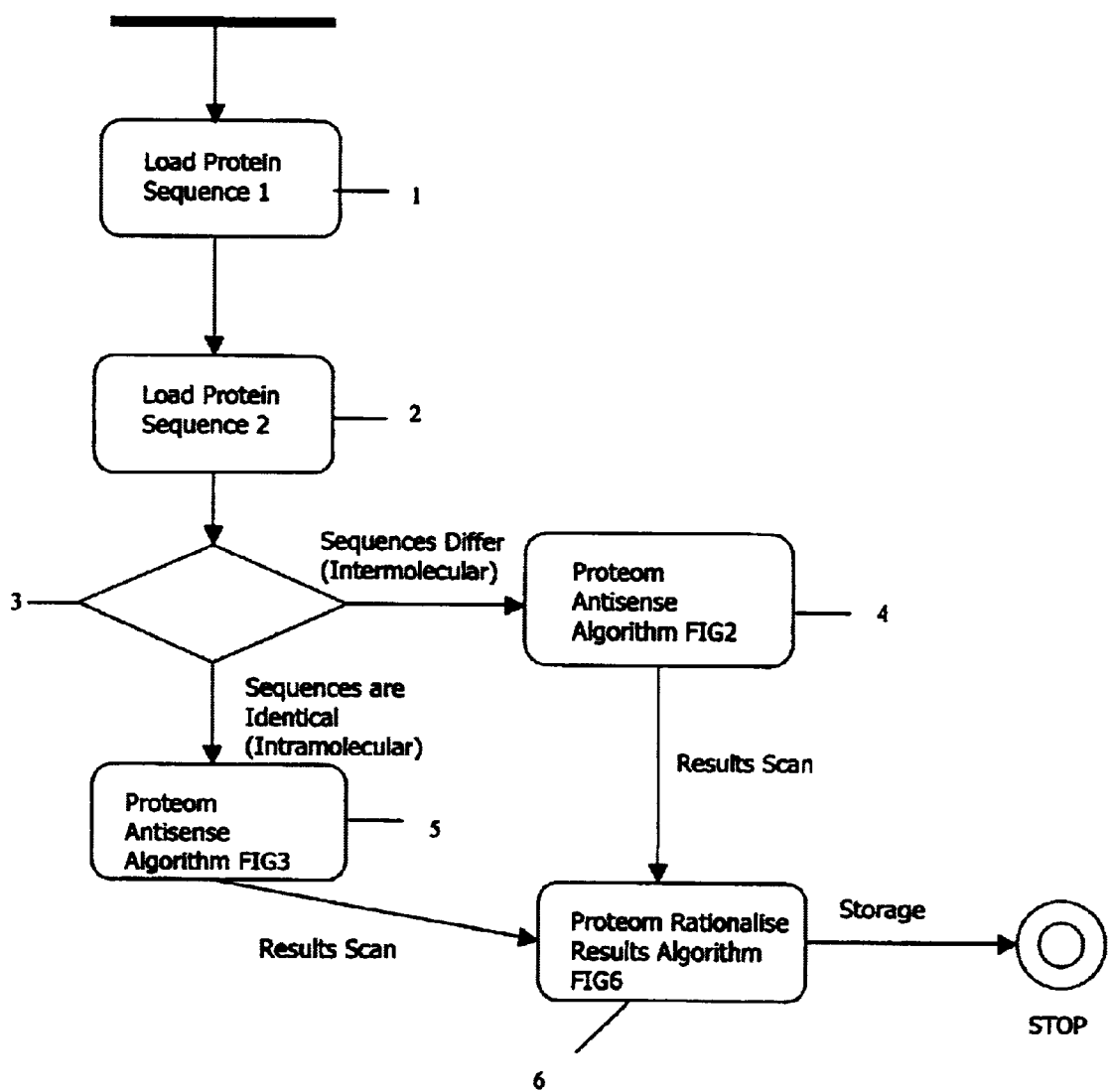

FIG. (2) shows a block diagram illustrating one embodiment for carrying out Step 4 in FIG. (1);

FIG. (3) shows a block diagram illustrating one embodiment for carrying out Step 5 in FIG. (1);

FIG. (4) shows a block diagram illustrating one embodiment for carrying out Step 8 in FIG. (2) and (3);

FIG. (5) shows a block diagram illustrating one embodiment for carrying out Step 8 in FIG. (2) and (3);

FIG. (6) shows a block diagram illustrating one embodiment for carrying out Step 6 in FIG. (1);

FIG. (7) shows a block diagram illustrating one embodiment of a method of the present invention;

FIG. (8) shows a block diagram illustrating one embodiment for carrying out Step 29 in FIG. (7);

FIG. (9) shows a block diagram illustrating one embodiment for carrying out Step 30 in FIG. (7);

FIG. (10) shows a diagram illustrating one embodiment of software design required to implement the ALS program;

FIG. (11) shows a diagram illustrating the principle of complementary peptide derivation. The amino acid sequence encoded by the minus or 'complementary' strand on DNA, when read in the 5'-3' direction, is known as a complementary peptide. The general scheme is illustrated in FIG. (11).

FIG. (12) shows a diagram to illustrate antisense amino acids pairings inherent in the genetic code; Amino acids are represented by single letter codes. 'Stop' indicates a stop codon. Solid lines connect sense—complementary amino acid (represented as one letter code) related residues. Non-polar residues are shaded, polar residues are in white (adapted from Mekler and Idlis, 1981).

FIG. (13) shows a representation of the Molecular Recognition Theory; and

FIG. (14) shows a graph and text illustrating biological data as an example of the utility of the ALS program. The program picked out antisense region LITVLNI (SEQ ID No. 8) in the IL-1R receptor. This peptide was shown to inhibit the biological activity of IL-1b in ESAP assay. The effect is dependent on the peptide sequence (see scrambled peptide LTILINV (SEQ ID No. 9)). The same effect is also seen in a Serum Amyloid IL-1 assay (i.e. assay independence). The peptide was shown to bind directly to IL-1 by using bio-sensing techniques.

A DESCRIPTION OF THE ANALYTICAL PROCESS OF THE INVENTION

The software, ALS (antisense ligand searcher), performs the following tasks:

Given the input of two amino acid sequences, calculates the position, number and probability of the existence of intra- (within a protein) and inter- (between proteins) molecular antisense regions. 'Antisense' refers to relationships between amino acids specified in Tables 2 and 4 (both 5'→3' derived and 3'→5' derived coding schemes).

Allows sequences to be inputted manually through a suitable user interface (UI) and also through a connection to a database such that automated, or batch, processing can be facilitated.

Provides a suitable database to store results and an appropriate interface to allow manipulation of this data.

Allows generation of random sequences to function as experimental controls.

Diagrams describing the algorithms involved in this software are shown in FIGS. 1–5.

DETAILED DESCRIPTION OF THE EMBODIMENTS

1. Overview

Figure 13:
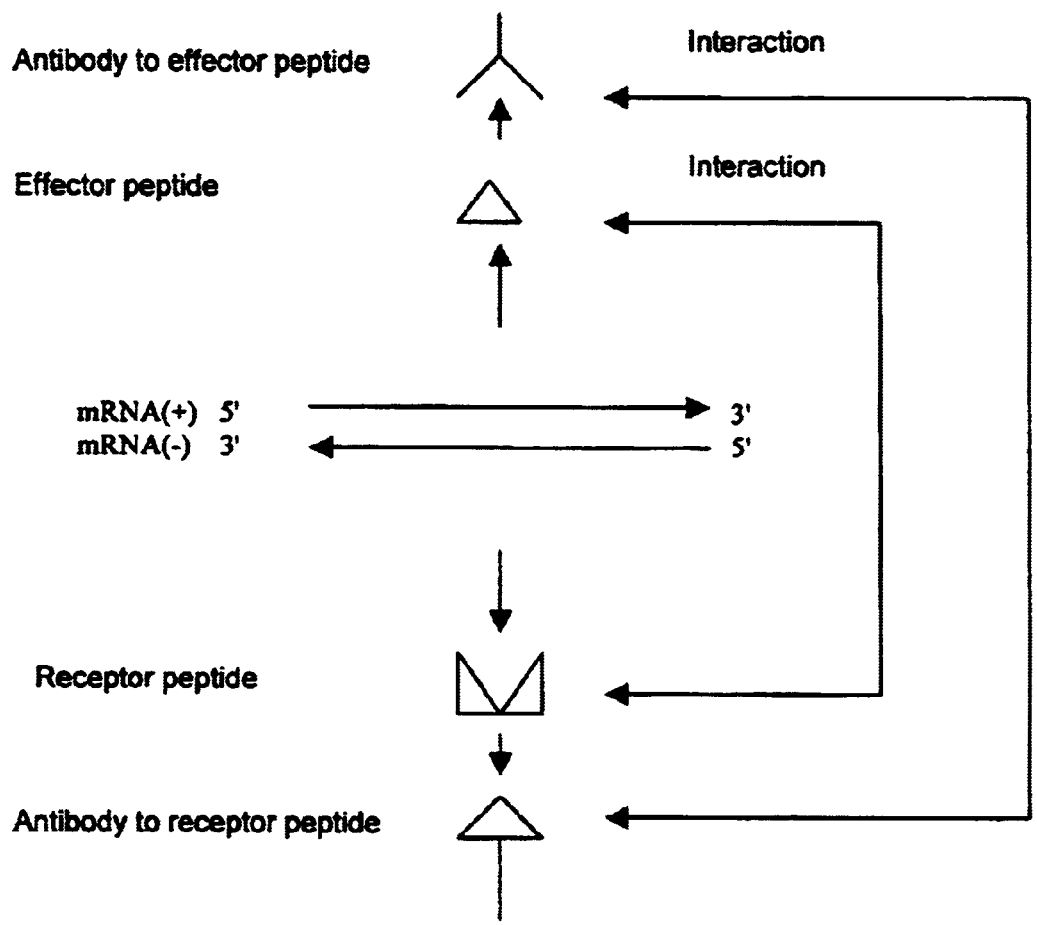

The present invention is directed toward a computer-based process, a computer-based system and/or a computer program product for analysing antisense relationships between protein or DNA sequences. A scheme of software architecture of a preferred embodiment is shown in FIG. 13.

The method of the embodiment provides a tool for the analysis of protein or DNA sequences for antisense relationships. This embodiment covers analysis of DNA or protein sequences for intramolecular (within the same sequence) antisense relationships or inter-molecular (between 2 different sequences) antisense relationships. This principle applies whether the sequence contains amino acid information (protein) or DNA information, since the former may be derived from the latter.

The overall process of the invention is to facilitate the batch analysis of an entire genome (collection of genes/and or protein sequences) for every possible antisense relationship of both inter- and intra-molecular nature. For the purpose of example it will be described here how a protein sequence database, SWISS PROT (Bairoch and Apweiler, 1999), may be analysed by the methods described.

SWISS PROT contains a list of protein sequences. The current invention does not specify in what format the input sequences are held—for this example we used a relational database to allow access to this data.

The program runs in two modes. The first mode (Intermolecular) is to select the first protein sequence in SWISS PROT and then analyse the antisense relationships between this sequence and all other protein sequences, one at a time. The program then selects the second sequence and repeats this process. This continues until all of the possible relationships have been analysed. The second mode (Intramolecular) is where each protein sequence is analysed for antisense relationships within the same protein and thus each sequence is loaded from the database and analysed in turn for these properties. Both operational modes use the same core algorithms for their processes. The core algorithms are described in detail below.

Figure 14:
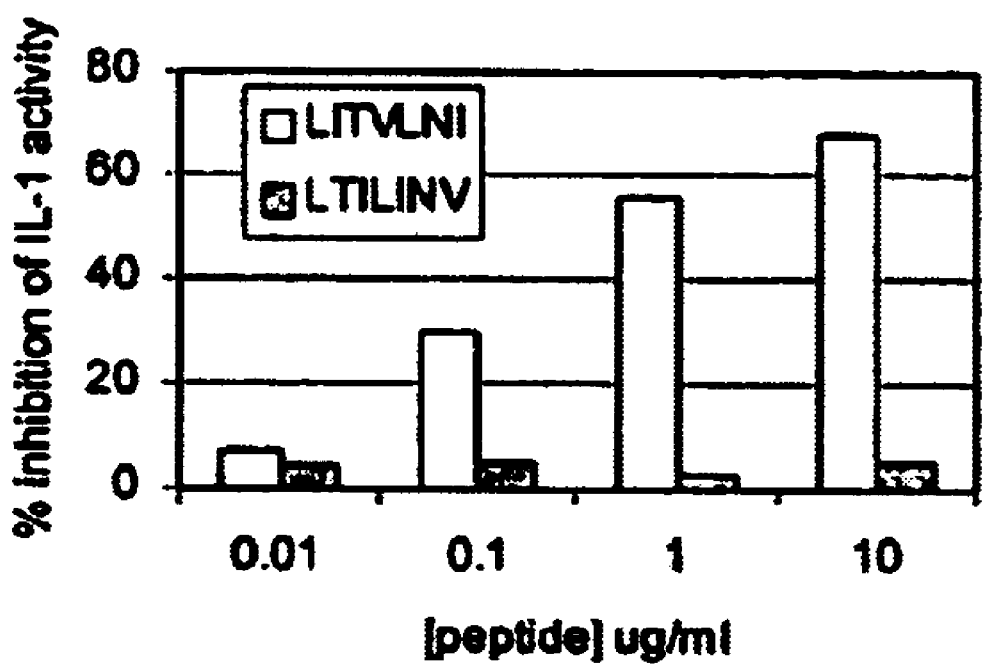

An example of the output from this process is shown in Table 7. Table 7 shows a list of proteins in the SWISS PROT database that contain highly improbable numbers of intramolecular antisense frames of size 10 (frame size is a section of the main sequence, it is described in more detail below). In Table 7 the total number of antisense frames are shown. Another way of representing this data is to list the actual sequence information itself. An example of the biological relevance of peptides derived from this method is shown in FIG. 14. The embodiment can output the data in either of these formats as well as many others.

2. Method of the Present Invention

For the purpose of example protein sequence 1 is ATR-GRDSRDERSDERTD (SEQ ID No. 1) and protein sequence 2 is GTFRTSREDSTYSGDTDFDE (SEQ ID No. 2) (universal 1 letter amino acid codes used).

In step 1 (see FIG. 1), a protein sequence, sequence 1, is loaded. The protein sequence consists of an array of universally recognised amino acid one letter codes, e.g. 'ADTRGSRD' (SEQ ID No. 3). The source of this sequence can be a database, or any other file type. Step 2, is the same operation as for step 1, except sequence 2 is loaded. Decision step 3 involves comparing the two sequences and determining whether they are identical, or whether they differ. If they differ, processing continues to step 4, described in FIG. 2, otherwise processing continues to step 5, described in FIG. 3.

Figure 6:
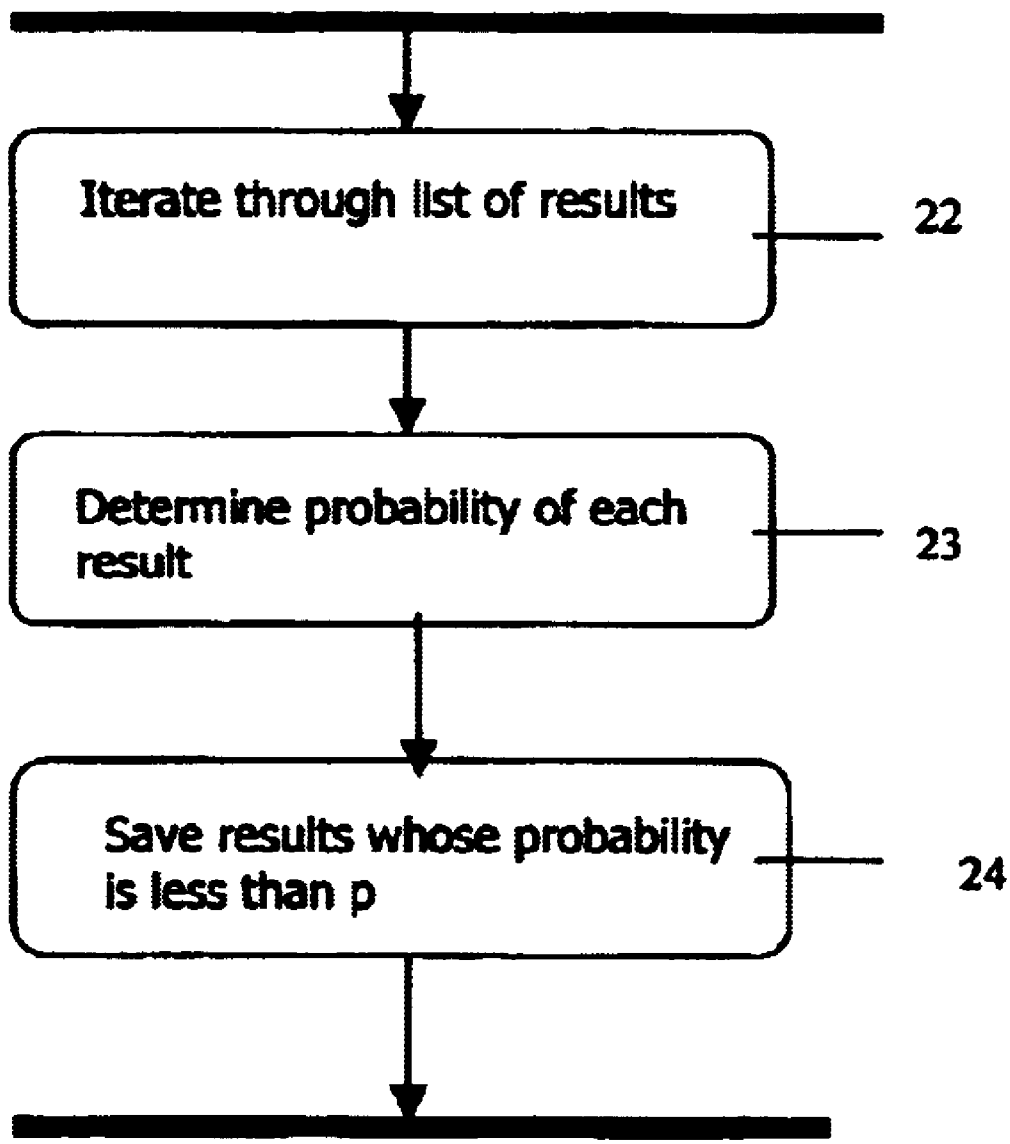

Step 6 analyses the data resulting from either step 4, or step 5, and involves an algorithm described in FIG. 6.

TABLE 5

Figure 2:
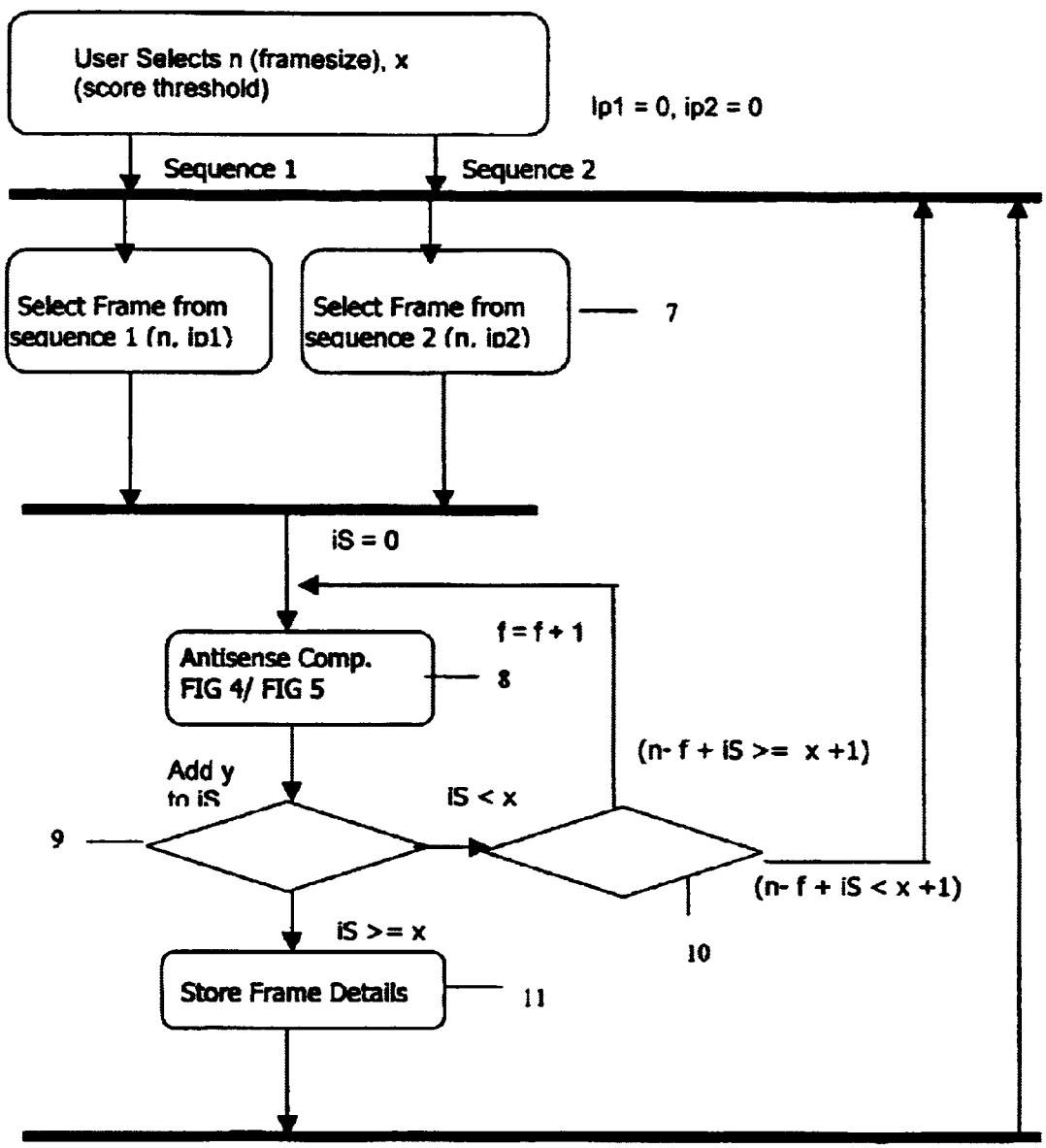

Description of parameters used in FIG. 2

| Name | Description |
|---|---|
| N | Framesize - the number of amino acids that make up each 'frame' |
| X | Score threshold - the number of amino acids that have to fulfil the antisense criteria within a given frame for that frame to be stored for analysis |
| Y | Score of individual antisense comparison (either 1 or 0) |
| IS | Running score for frame - (sum of y for frame) |
| Ip1 | Position marker for Sequence 1 - used to track location of selected frame for sequence 1 |
| Ip2 | Position marker for Sequence 2 - used to track location of selected frame for sequence 1 |
| F | Current position in frame |

In Step 7, a 'frame' is selected for each of the proteins selected in steps 1 and 2. A 'frame' is a specific section of a protein sequence. For example, for sequence 1, the first frame of length '5' would correspond to the characters 'ATRGR' (SEQ ID No. 4). The user of the program decides the frame length as an input value. This value corresponds to parameter 'n' in FIG. 2. A frame is selected from each of the protein sequences (sequence 1 and sequence 2). Each pair of frames that are selected are aligned and frame position parameter f is set to zero. The first pair of amino acids are 'compared' using the algorithm shown in FIG. 4/FIG. 5. The score output from this algorithm (y, either one or zero) is added to a aggregate score for the frame is. In decision step 9 it is determined whether the aggregate score iS is greater than the Score threshold value (x). If it is then the frame is stored for further analyisis. If it is not then decision step 10 is implemented. In decision step 10, it is determined whether it is possible for the frame to yield the score threshold (x). If it can, the frame processing continues and f is incremented such that the next pair of amino acids are compared. If it cannot, the loop exits and the next frame is selected. The position that the frame is selected from the protein sequences is determined by the parameter ip1 for sequence 1 and ip2 for sequence 2 (refer to FIG. 2). Each time steps 7 to 10 or 7 to 11 are completed, the value of ip1 is zeroed and then incremented until all frames of sequence 1 have been analysed against the chosen frame of sequence 2. When this is done, ip2 is then incremented and the value of ip1 is incremented until all frames of sequence 1 have been analysed against the chosen frame of sequence 2. This process repeats and terminates when ip2 is equal to the length of sequence 2. Once this process is complete, sequence 1 is reversed programmatically and the same analysis as described above is repeated. The overall effect of repeating steps 7 to 11 using each possible frame from both sequences is to facilitate step 8, the antisense scoring matrix for each possible combination of linear sequences at a given frame length.

Figure 3:
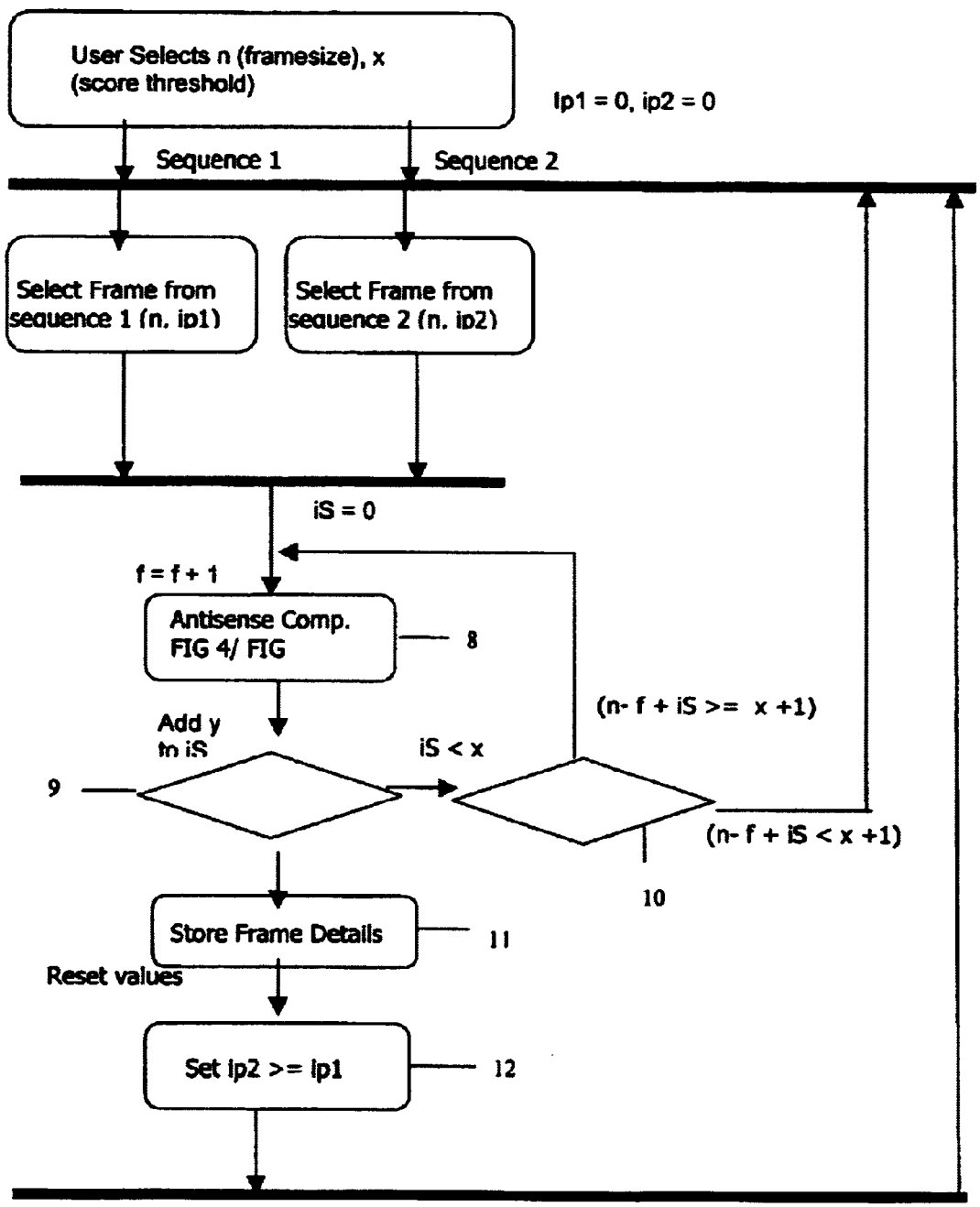

FIG. 3 shows a block diagram of the algorithmic process that is carried out in the conditions described in FIG. 1. Step 12 is the only difference between the algorithms FIG. 2 and FIG. 3. In step 12, the value of ip2 (the position of the frame in sequence 2) is set to at least the value of ip1 at all times since as sequence 1 and sequence 2 are identical, if ip2 is less than ip1 then the same sequences are being searched twice.

Figure 4:
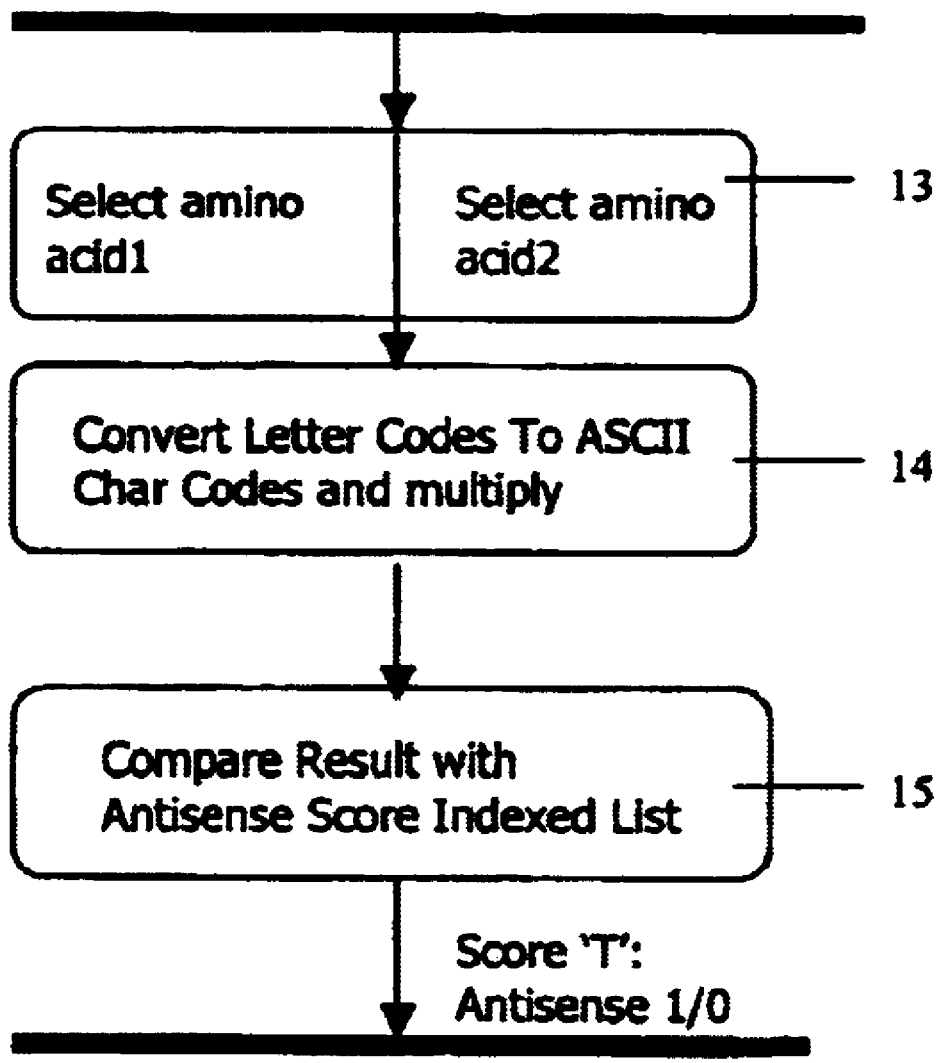
Figure 5:
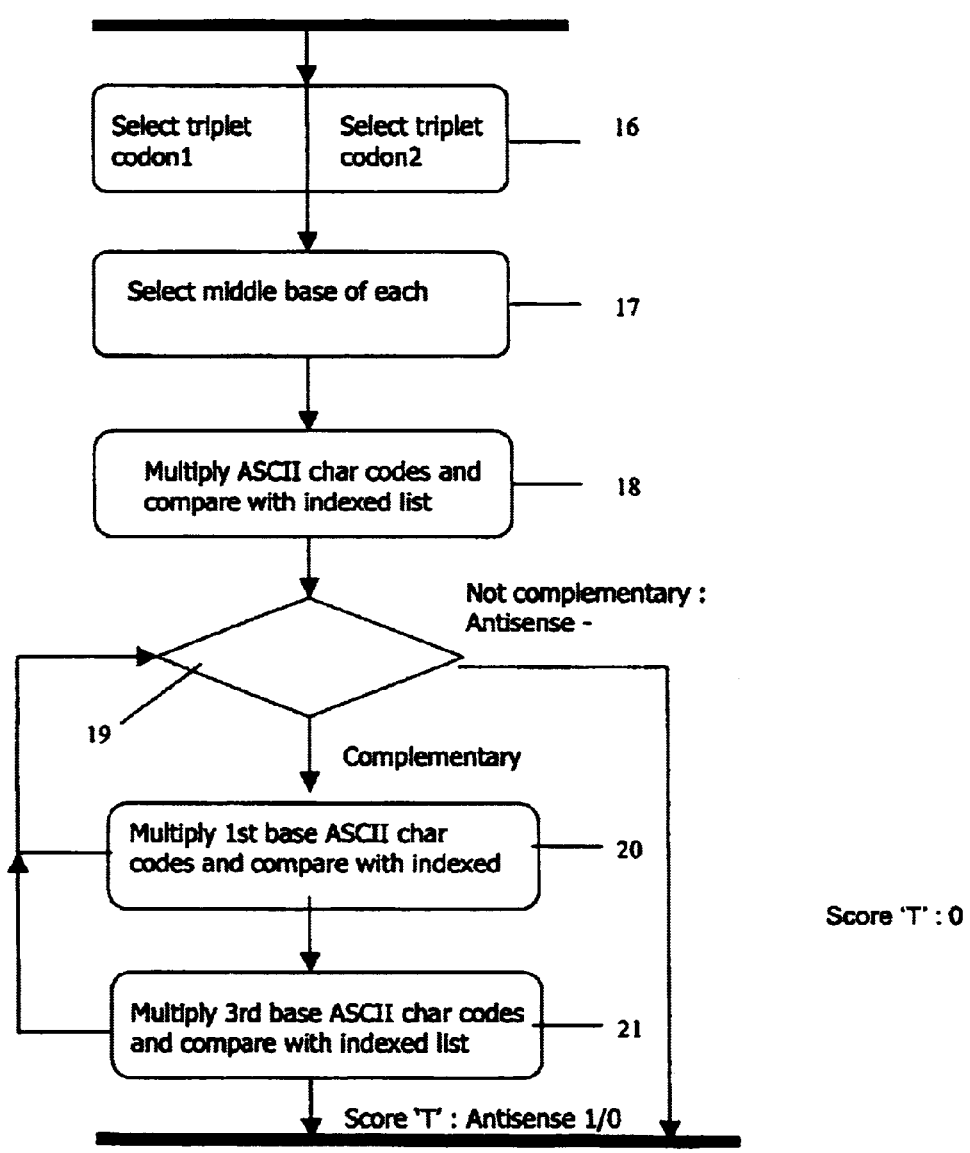

FIGS. 4 and 5 describe the process in which a pair of amino acids (FIG. 4) or a pair of triplet codons are assessed for an antisense relationship. The antisense relationships are listed in Tables 2 and 4. In step 13, the currently selected amino acid from the current frame of sequence 1 and the currently selected amino acid from the current frame of sequence 2 (determined by parameter 'f' in FIGS. 2/3) are selected. For example, the first amino acid from the first frame of sequence 1 would be 'A' and the first amino acid from the first frame of sequence 2 would be 'G'. In step 14, the ASCII character codes for the selected single uppercase characters are determined and multiplied and, in step 15, the product compared with a list of precalculated scores, which represent the antisense relationships in Tables 2 and 4. If the amino acids are deemed to fulfil the criteria for an antisense relationship (the product matches a value in the precalculated list) then an output parameter 'T' is set to 1, otherwise the output parameter is set to zero.

Steps 16–21 relate to the case where the input sequences are DNA/RNA code rather the protein sequence. For example sequence 1 could be AAATTTAGCATG (SEQ ID No. 5) and sequence 2 could be TTTAAAMGCATGC (SEQ ID No. 6). The domain of the current invention includes both of these types of information as input values, since the protein sequence can be decoded from the DNA sequence, in accordance with the genetic code. Steps 16–21 determine antisense relationships for a given triplet codon. In step 16, the currently selected triplet codon for both sequences is 'read'. For example, for sequence 1 the first triplet codon of the first frame would be 'AAA', and for sequence 2 this would be 'TTT'. In step 17, the second character of each of these strings is selected. In step 18, the ASCII codes are multiplied and compared, in decision step 19, to a list to find out if the bases selected are 'complementary', in accordance with the rules of the genetic code. If they are, the first bases are compared in step 20, and subsequently the third bases are compared in step 21. Step 18 then determines whether the bases are 'complementary' or not. If the comparison yields a 'non-complementary' value at any step the routine terminates and the output score 'T' is set to zero. Otherwise the triplet codons are complementary and the output score T=1.

FIG. 6 illustrates the process of rationalising the results after the comparison of 2 protein or 2 DNA sequences. In step 22, the first 'result' is selected. A result consists of information on a pair of frames that were deemed 'antisense' in FIGS. 2 or 3. This information includes location, length, score (i.e., the sum of scores for a frame) and frame type (forward or reverse, depending on orientation of sequences with respect to one another). In step 23, the frame size, the score values and the length of the parent sequence are then used to calculate the probability of that frame existing. The statistics, which govern the probability of any frame existing, are described in the next section and refer to equations 1–4. If the probability is less than a user chosen value 'p', then the frame details are 'stored' for inclusion in the final result set (step 24).

Statistical Basis of Program Operation

The number of complementary frames in a protein sequence can be predicted from appropriate use of statistical theory.

The probability of any one residue fitting the criteria for a complementary relationship with any other is defined by the groupings illustrated in EXAMPLE 2. Thus, depending on the residue in question, there are varying probabilities for the selection of a complementary amino acid. This is a result of an uneven distribution of possible partners. For example possible complementary partners for a tryptophan residue include only proline whilst glycine, serine, cysteine and arginine all fulfil the criteria as complementary partners for threonine. The probabilities for these residues aligning with a complementary match are thus 0.05 and 0.2 respectively. The first problem in fitting an accurate equation to describe the expected number of complementary frames within any sequence is integrating these uneven probabilities into the model. One solution is to use an average value of the relative abundance of the different amino acids in natural sequences. This is calculated by equation 1

$$v = \Sigma R * N \quad\quad\quad 1$$

Where v=probability sum, R=fractional abundance of amino acid in *e.coli* proteins, N=number of complementary partners specified by genetic code.

This value (v) is calculated as 2.98. The average probability (p) of selecting a complementary amino acid is thus 2.98/20=0.149.

For a single 'frame' of size (n) the probability (C) of pairing a number of complementary amino acids (r) can be described by the binomial distribution (equation 2)

$$C = \frac{n!}{(n-r)!r!} p^r (1-p)^{(n-r)} \quad\quad\quad 2$$

With this information we can predict that the expected number (Ex) of complementary frames in a protein to be:

$$Ex = 2(S-n)^2 \frac{n!}{(n-r)!r!} p^r (1-p)^{(n-r)} \quad\quad\quad 3$$

Where S=protein length, n=frame size, r=number of complementary residues required for a frame and p=0.149. If r=n, representing that all amino acids in a frame have to fulfil a complementary relationship, the above equation simplifies to:

$$Ex = 2(S-n)^2 p^n \quad\quad\quad 4$$

For a population of randomly assembled amino acid chains of a predetermined length we would expect the number of frames fulfilling the complementary criteria in the search algorithm to vary in accordance with a normal distribution.

Importantly, it is possible to standardise results such that given a calculated mean ($\mu$) and standard deviation ($\sigma$) for a population it is possible to determine the probability of any specific result occurring. Standardisation of the distribution model is facilitated by the following relation:

$$Z = \frac{X - \mu}{\sigma} \quad\quad\quad 5$$

Where X is a single value (result) in a population.

If we are considering complementary frames with a single protein structure then the above statistical model requires further analysis. In particular, the possibility exists that a region may be complementary to itself, as indicated in the diagram below.

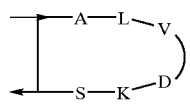

Reverse turn motifs within proteins. A region of protein may be complementary to itself. In this scenario, A-S, L-K and V-D are complementary partners. A six amino acid wide frame would thus be reported (in reverse orientation). A frame of this type is only specified by half of the residues in the frame. Such a frame is called a reverse turn.

In this scenario, once half of the frame length has been selected with complementary partners, there is a finite probability that those partners are the sequential neighbouring amino acids to those already selected. The probability of this occurring in any protein of any sequence is:

$$Ex = p^{f/2}(S-f) \quad\quad\quad 7$$

Where f is the frame size for analysis, and S is the sequence length and p is the average probability of choosing an antisense amino acid.

The software of the embodiment incorporates all of the statistical models reported above such that it may assess whether a frame qualifies as a forward frame, reverse frame, or reverse turn.

Antisense X-Ray Structure Analysis (AXRA) Software

Currently over 20 prokaryote and 1 eukaryote genomes have been completely sequenced and more than 3 times that number are in progress or nearing completion including the human genome. The wealth of information generated is providing the foundation for a new important initiative in structural biology. Protein fold assignment and homology modelling of related protein structures have become important research tools, providing structural insights for many different areas of biology and medicine, Burley et al., 1999. At present, however, despite large-scale protein structure analyses only a fraction of a protein can usually be modelled e.g. 18% of all residues, or domains in yeast proteins.

"The obvious solution to this problem is to obtain complete three-dimensional structural information for each distinct protein fold. De novo prediction of a protein structure from its sequence is simply not feasible at present", Burley et al, 1999.

The current invention provides a novel method for aiding the determination of three dimensional structure.

This software performs the following tasks:

Reads an X-Ray structure file

Determines regions of complementary hydropathy and /or antisense pairings in 3D space, between
1) 2 discontinuous protein sequences
2) 1 discontinuous and 1 linear protein sequences
3) 2 linear protein sequences.

Inventive Aspect of Software

The observation that many receptor-ligand contact points within the IL-1β II-1R X-ray crystal structure involve an interchange of residues of opposite polarity, suggests that this may represent a general principle of protein contact points. In this vein, AXRA was designed to analyse X-ray data for regions of complementary hydropathy and/or antisense relationships between proximal residues. This software confers significant advantages in:

Prediction of tertiary and quaternary protein structures.
Prediction of intermolecular contact points AXRA overcomes previous limitations of analysing protein sequences for antisense interactions by recognising for the first time that antisense pairings also exist in discontinuous regions of proteins, and thus antisense sequence searching can be expanded to 3 dimensional structures.

Program Operation

In overview, program functions by:
Reading an X-ray data file
Calculating which sets of residues, or 'frames' of user defined length, represent the greatest area of complementary hydropathy and/or antisense relationships.

User options allow control over searching parameters such as frame length, minimum distance for partner and number of neighbouring residues from the same chain to exclude from analysis.

TABLE 6

Description of parameters used in AXRA process

| Name | Description |
|---|---|
| N | Framesize |
| Pos | Current index in a sequence array (one letter amino acid codes) |
| Mind | A minimum distance parameter - used with maxd to determine the range of distance values that will be used to locate neighboring amino acids. |
| Maxd | A maximum distance parameter - used with mind to determine the range of distance values that will be used to locate neighboring amino acids. |
| X | Maximum number of amino acids that can exist within a Nearest Neighbour Sphere (NNS). |
| ST | Score Threshold - when analysing frames of the protein sequence the score threshold determines the number of amino acids within a frame that have to exist for that frame to be counted as a 'hit' |
| S | Score - the aggregate score of antisense relationships within a frame |
| HST | HydropathyScoreThreshold - a user input value determining the threshold hydropathy score (determining whether a frame is saved or not). |
| LR | List of arrays of hydropathy scores. Each amino acid has a list of hydropathy scores relating to the list of nearest neighbour (NNS) amino acids. |
| RF | Result Frame - a frame containing hydropathy scores. |

Figure 7:
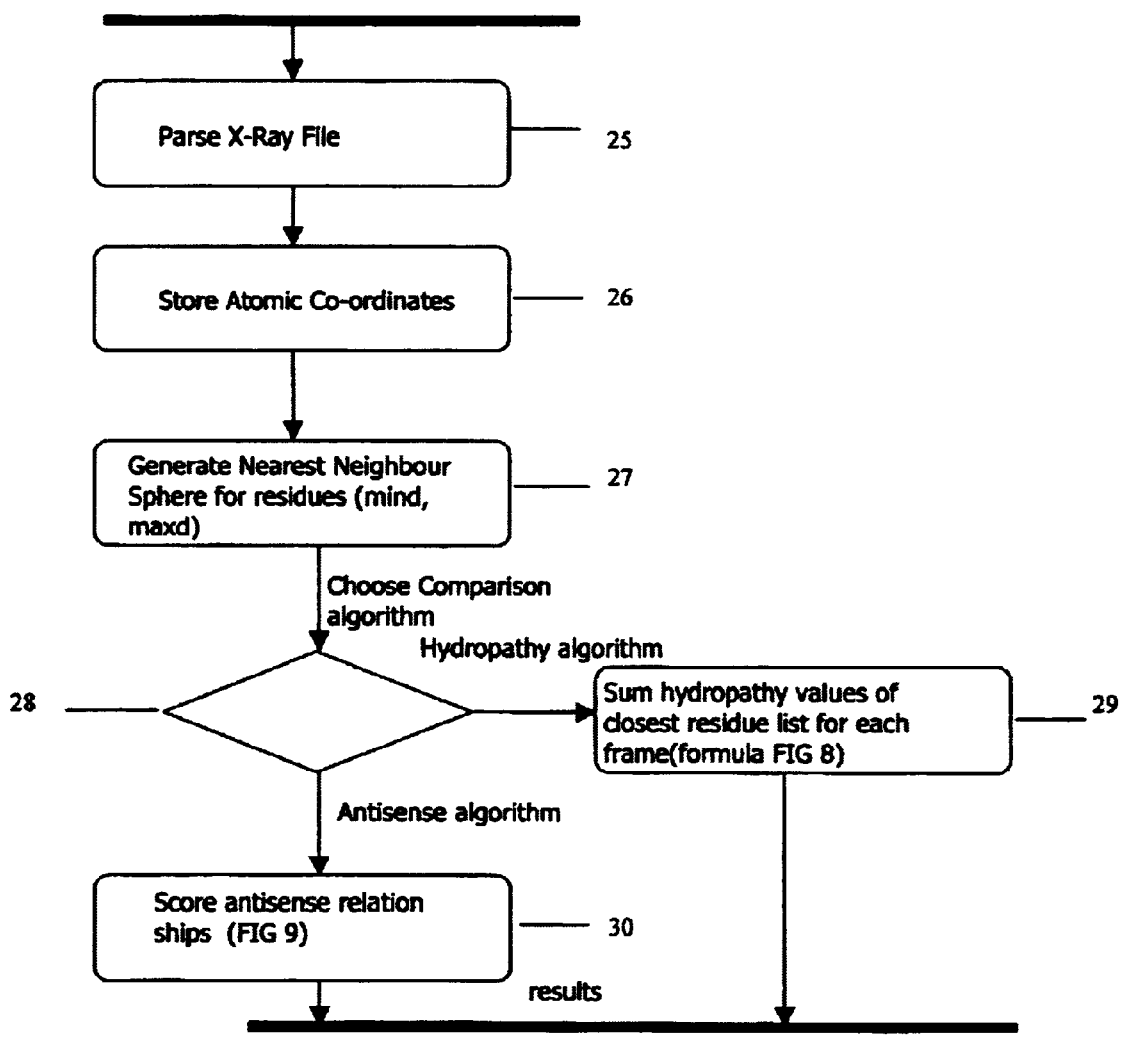

Decision steps 25 to 30 are shown in FIG. 7. In step 25, the program reads a file containing the Cartesian x, y, z co-ordinates of a protein structure and these are stored by conventional programmatic means (step 26). The protein sequence (1 letter amino acid codes) is also read from this file and stored in memory as an array of characters. In step 27, the distances between each alpha- carbon atom (as denoted in Brookhaven databank format CA) and all other carbon atoms that make up each amino acid (CB, c1, c2, cn) are calculated by vector mathematics from the cartesian co-ordinates. The program user chooses (through the UI) which atom type (e.g. CB, c1 etc) are used in the calculation of the distances between two amino acids. The x closest amino acids for each residue are stored for further analysis. The value x, the number of nearest amino acids to interrogate, is provided by the user from a suitable user interface (UI). For each amino acid in the protein structure we now have a list of proximal amino acids within distances mind and maxd between any carbon atoms that constitute the structure of that residue. The default maximum distance in this process is 15 angstroms; if less than x amino acids fall within this distance then only those within this distance will be stored. The user may change this value through the UI. This is known as the Nearest Neighbour Sphere (NNS). In decision step 28, the program flow follows the user's choice (input through the UI) as to whether the analysis should be based on hydropathy (step 29) or whether the analysis should be based on antisense relationships (step 30).

Figure 8:
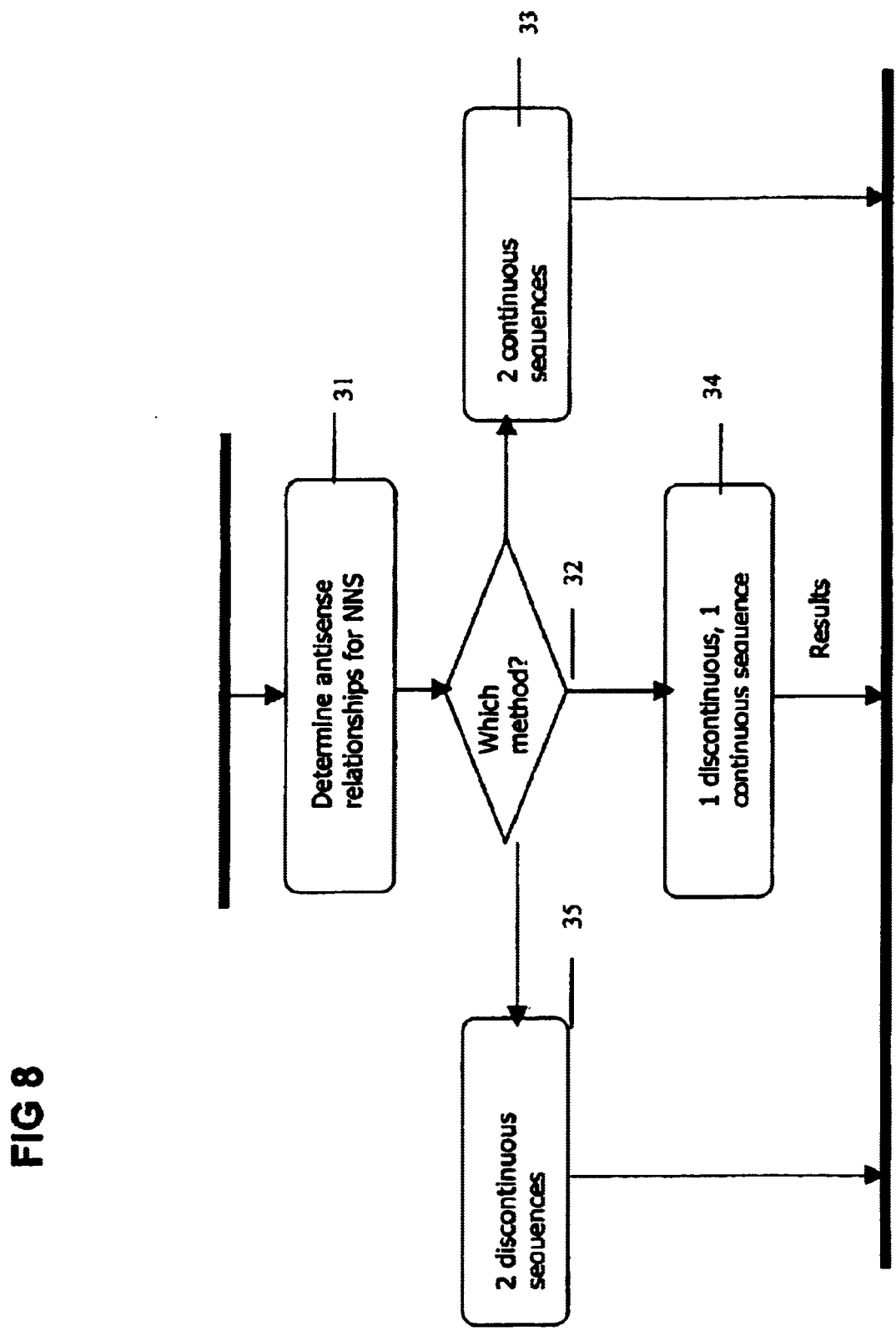

Decision steps 31 to 35 are shown in FIG. 8. In step 31, the antisense relationships between the first amino acid in the protein sequence (stored in step 25) and the list of amino acids stored as the nearest neighbour sphere (NNS) are determined. (Programmatically, the NNS is a list of arrays—one array for each position in the protein sequence). To do this, each amino acid in the sequence is selected in turn and compared with each member of its NNS (stored in step 27) using the algorithm depicted in FIG. 5. If none of the NNS members for a particular amino acid show an antisense relationship (i.e. output value of 1 from FIG. 5) then a zero value is scored at this position in a Result Array 'R', otherwise the details (sequence index) of the closest amino acid fulfilling an antisense relationship are stored in the result Array 'R' for further analysis. The user may specify input values determining the maximum (maxd) and minimum (mind) distances that antisense relationships must fall within to be accepted. This process is repeated for all amino acids in the protein sequence generating a Result Array 'R' containing sequence indexes of all amino acids that fulfil an antisense criteria within the NNS. The overall process here is to define which proximal amino acids have antisense relationships.

Decision step 32 routes the users selection (from the UI) of whether to find regions of antisense relationships between 2 continuous parts of the same sequence (step 33), 1 continuous and 1 discontinuous part of the same sequence (step 34) or 2 discontinuous parts of the same sequence (step 35).

In step 33, the first 'frame' of length 'n' of the protein sequence is selected. The frame is a section of the total sequence, and the length of this frame (n) is chosen by the user through the UI. Also chosen through the UI is a ScoreThreshold' 'ST' parameter. The first frame (of length 'n') is selected from the protein sequence. For each amino acid in this frame the NNS is analysed. If any continuous combinations of antisense relationships within the NNS are found where the aggregate score 'S' is greater than the user chosen ScoreThreshold 'ST' then the amino acids sequence locations are stored as a 'hit' frame. This is repeated for each frame in the protein sequence. When the process has finished the 'hit frame' results are then listed in an appropriate UI format.

In step 34, the first 'frame' of length 'n' of the protein sequence is selected. The frame is a section of the total sequence, and the length of this frame (n) is chosen by the user through the UI. Also chosen through the UI is a ScoreThreshold' 'ST' parameter. The first frame (of length 'n') is selected from the protein sequence. For each amino acid in each frame the NNS is analysed. If any discontinuous combinations of antisense relationships within the NNS are found where the aggregate score 'S' is greater than the user chosen ScoreThreshold 'ST' then the amino acids sequence locations are stored as a 'hit' frame. This is repeated for each frame of the protein sequence. When the process has finished the 'hit frame' results are then listed in an appropriate UI format.

In step 35, the first amino acid of the protein sequence is selected. The list of antisense relationships determined in step 31 is listed in an appropriate UI format.

Figure 9:
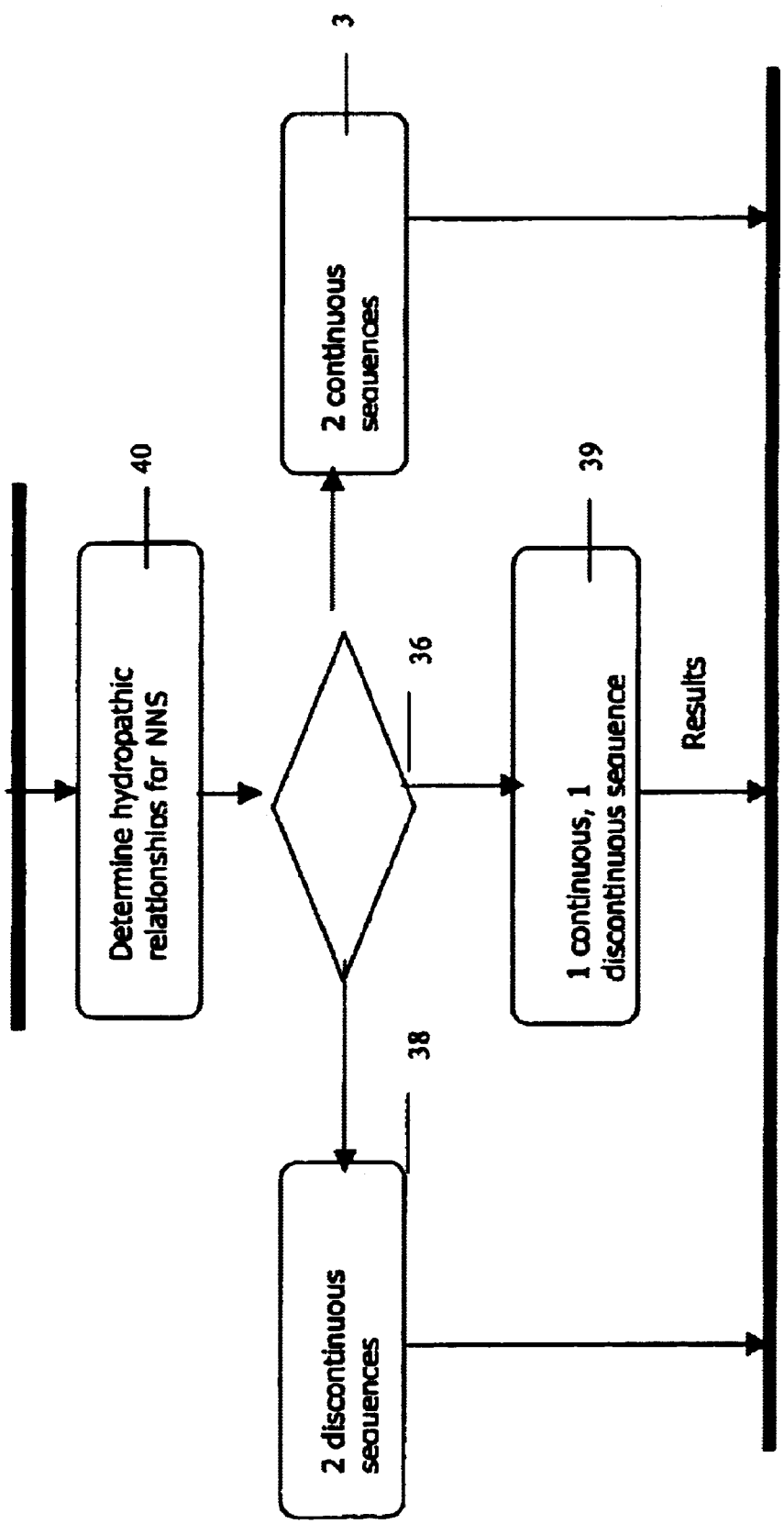
Figure 10:
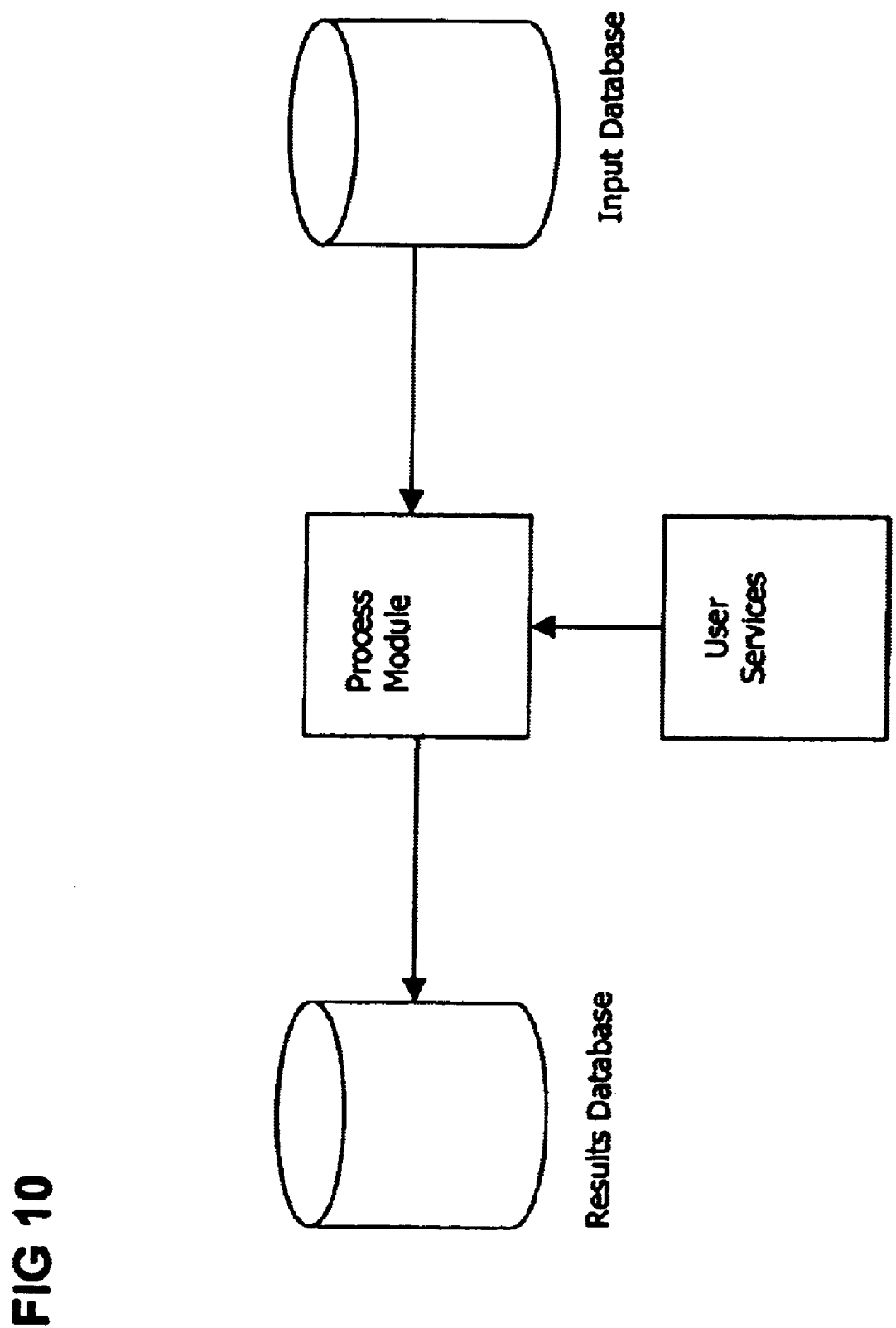
Figure 11:
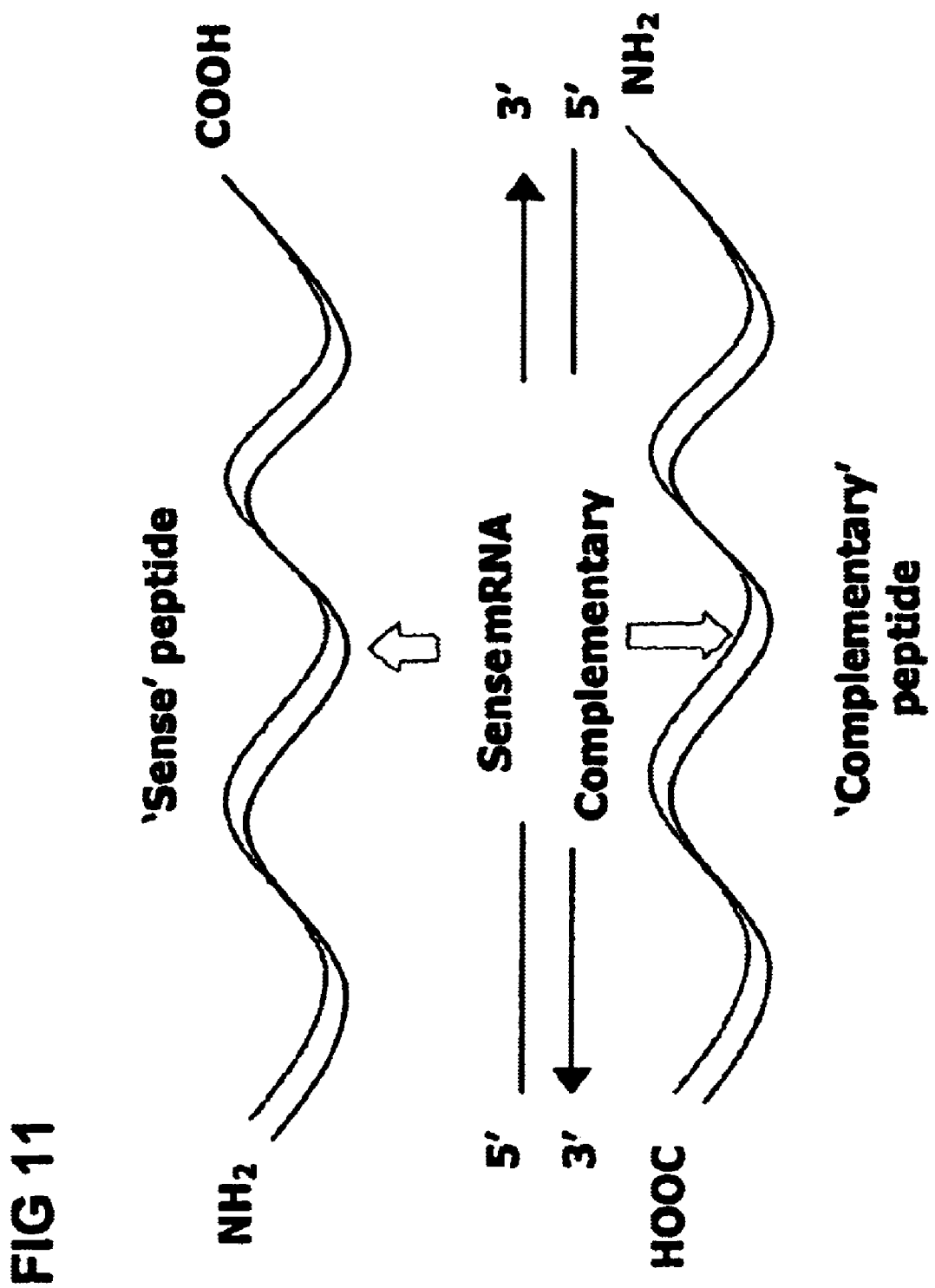
Figure 12:
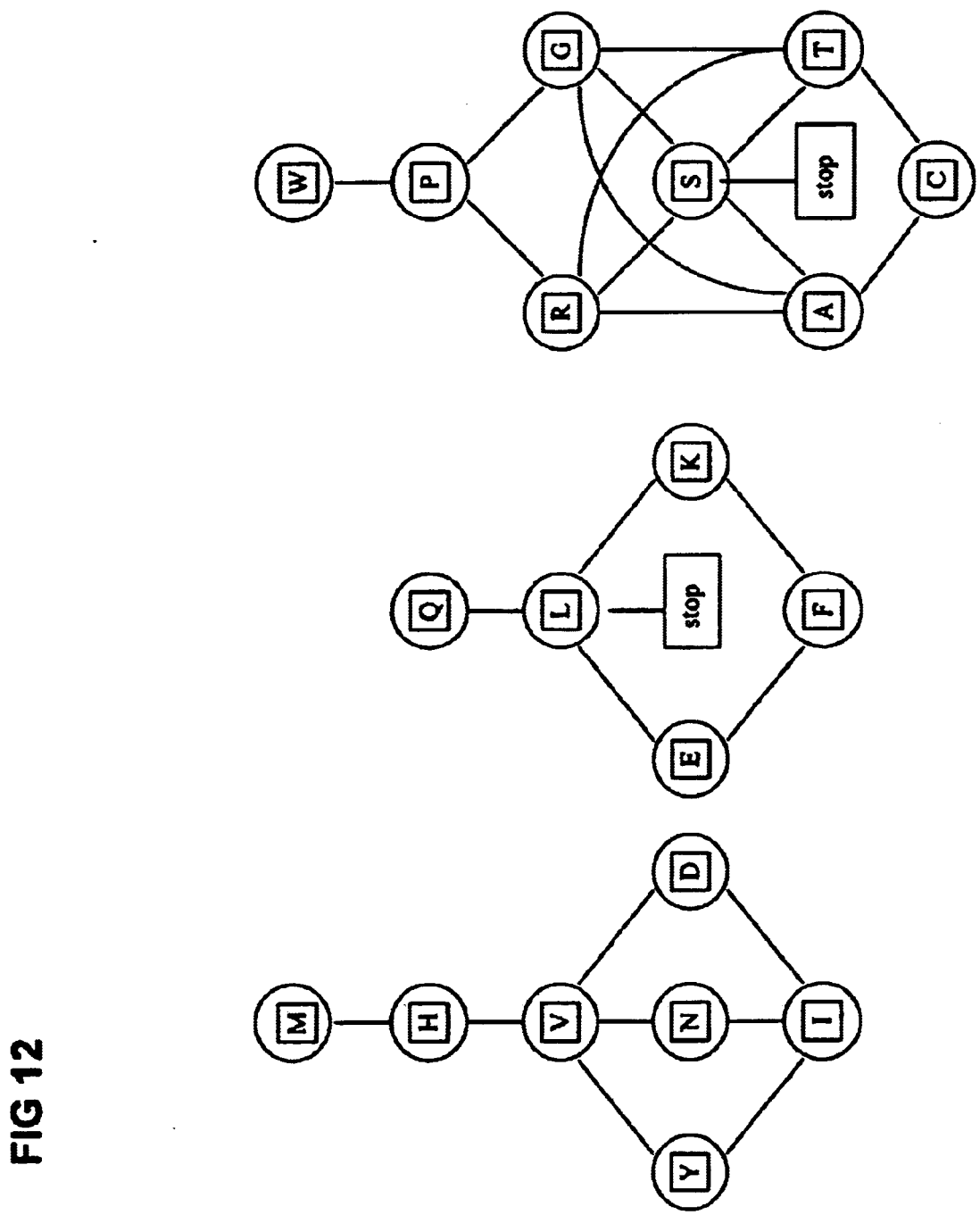

Decision steps 36 to 40 are shown in FIG. 9. In step 40, the hydropathic comparison scores between the first amino acid in the protein sequence (stored in step 25) and the list of amino acids stored as the nearest neighbour sphere (NNS) are determined using the following equation:

$$H = (a_1 + a_2)^2$$

Where a1 and a2 are the hydropathy scores of the amino acids selected as scored on the Kyte and Doolittle scale (Kyte and Doolittle, 1982). This equation is evaluated for each pair of amino acids specified by the currently selected amino acid and its partners in the NNS and the resulting H values are scored.

The user may specify input values determining the maximum (maxd) and minimum (maxd) distances that relationships must fall within to be processed further. This process is repeated for all amino acids in the protein sequence. The overall process here is to define the hydropathic relationships between proximal amino acids. Programmatically, we end up with a list of arrays where each array contains a list of hydropathic scores for amino acids neighbouring the amino acid specified by the index in the main list. This list of arrays LR is then used for steps 37, 38 or 39.

Decision step 36 routes the users selection (from the UI) of whether to find regions of complementary hydropathy between 2 continuous parts of the same sequence (step 37), 1 continuous and 1 discontinuous part of the same sequence (step 38) or 2 discontinuous parts of the same sequence (step 39).

In step 37, the frame is a section of the total sequence, and the length of this frame (n) is chosen by the user through the UI. Also chosen through the UI is a Hydropathy Score Threshold 'HST' parameter. The first 'frame' of length 'n' of the protein sequence is selected. In this first frame the first amino acid is selected. The LOWEST value of the list of hydropathy scores formed in step 40 is taken and written to a result frame RF. (The sequence indexes of the amino acids that are responsible for the lowest scores are written to another list SL such that a link between amino acid location and hydropathy is created.). This is repeated for each amino acid in the frame until we have a completed result Frame 'RF' that contains a list of the lowest hydropathy scores available for the specified amino acids. The average hydropathy for this frame is then determined by the following equation:

$$\Omega = \sqrt{\frac{\sum H}{L}} \qquad 10$$

Where H is defined in the equation above, L is the frame length, denoting the length of the amino acid sequence that is used for the comparison. The lower the score ($\Omega$), the greater the degree of hydropathic complementarity for the defined region.

Once the average hydropathy score is calculated, if that score is LOWER than the HST parameter the sequence indexes of the amino acids that were responsible for the hydropathy values used in equation 10 are analysed for continuity (i.e. are these amino acids continuous, such as pos 10, pos 11, pos 12 etc). If continuity is found, the frame is stored for further analysis.

This is repeated for each frame of the protein sequence (i.e. of frame length 7, 1–7, 2–8, 3–9 etc). When the process has finished the results are then listed in an appropriate UI format.

In step 39, the frame is a section of the total sequence, and the length of this frame (n) is chosen by the user through the UI. Also chosen through the UI is a Hydropathy Score Threshold 'HST' parameter. The first 'frame' of length 'n' of the protein sequence is selected. In this first frame the first amino acid is selected. The LOWEST value of the list of hydropathy scores formed in step 40 is taken and written to a result frame RF. (The sequence indexes of the amino acids that are responsible for the lowest scores are written to another list SL such that a link between amino acid location and hydropathy is created.). This is repeated for each amino acid in the frame until we have a completed result Frame 'RF' that contains a list of the lowest hydropathy scores available for the specified amino acids. The average hydropathy for this frame is then determined by the following equation 10.

Once the average hydropathy score is calculated, if that score is LOWER than the HST parameter the sequence indexes of the amino acids that were responsible for the hydropathy values used in equation 10 are stored in a suitable programmatic container to display as results. This is repeated for each frame of the protein sequence (i.e. of frame length 7, 1–7, 2–8, 3–9 etc). When the process has finished the results are then listed in an appropriate UI format.

In step 38, all hydropathic relationships (equation 10) between each amino acid and its NNS counterparts are written out to a display for further analysis.

The program flow is illustrated in FIG. 7.

Specific Example of AXRA Output

The software was used to select regions of complementary hydropathy within the IL-1β IL-1R crystal structure. The program was run on the X-ray file (pdb2itb) and selected the most complementary region between the ligand and receptor as consisting of residues 47–54 of IL-1β (sequence QGEESND, SEQ ID No. 7) and residues 245, 244, 303, 298, 242, 249, 253 of the receptor (sequence W, S, V, I, G, Y, N). This demonstrates two things. Firstly, it shows that the software functions properly in that it can locate regions of hydropathic complementarity between a receptor-ligand pair. Secondly, it proves that the region of IL-1β which has the closest residues of greatest hydropathic inversion to the IL-1 type I receptor is the trigger loop region of IL-1β to which we have previously designed antisense peptides.

UTILITY OF THE INVENTION

This invention presents a novel informatics technology that greatly accelerates the pace for initial identification and subsequent optimization of small peptides that bind to protein-protein targets. Using this technology an operator can systematically produce large numbers or 'catalogues' of small peptides that are very useful and specific agonists/antagonists of protein-protein interactions.

These peptides are ideally suited for use in drug discovery programs as biological tools for probing gene function, or as a basis for configuring drug discovery screens or ba molecular scaffold for medicinal chemistry. In addition, peptides with a high affinity for a protein could form drugs in their own right.

Finally, these peptides are amenable to dramatic further improvement through various methods in addition to traditional medicinal chemistry.

The publications, patents, and patent applications listed herein are incorporated by reference in their entirety.

REFERENCES

The publications, patents, and patent applications cited are incorporated by reference herein in their entirety.

Aota S, Gojobori T, Ishibashi F, Marvyama T and Ilkarnea T. 1988. Codon usage tabulated from the GenBank Genetic Sequence Data. Nucleic Acid Res. 16: 315–391.

Bairoch A and Apweiler R. 1999. The SWISS-PROT protein sequence data bank and its supplement TrEMBL in 1999. Nucleic Acids Research. 27:49–54.

Biro J. 1981. Comparative analysis of specificity in protein-protein interactions. Part II.:

The complementary coding of some proteins as the possible source of specificity in protein-protein interactions. Med.Hypotheses 7: 981–993.

Blalock J E. 1995. Genetic origins of protein shape and interaction rules. Nature Medicine 1: 876–878.

Blalock J E and Smith E M. 1984. Hydropathic anti-complementarity of amino acids based on the genetic code. Biochem Biophys Res Commun. 12: 203–7.

Baranyi L, Campbell W, Ohshima K, Fujimoto S, Boros M and Okada H. 1995. The antisense homology box: a new motif within proteins that encodes biologically active peptides. Nature Medicine. 1:894–901.

Baranyi L, Campbell W and Okada H. 1996. Antisense homology boxes in C5a receptor and C5a anaphylatoxin: a new method for identification of potentially active peptides. J Immunol. 157:4591–601.

Bost K L, Smith E M. and Blalock J E.1985. Similarity between the corticotropin (ACTH) receptor and a peptide encoded by an RNA that is complementary to ACTH mRNA. Proc.Natl. Acad. Sci. USA 82: 1372–1375.

Bost K L and Blalock J E. 1989. Production of anti-idiotypic antibodies by immunization with a pair of complementary peptides. J. Molec. Recognit. 1: 179–183.

Burley S K, Almo S C, Bonanno J B, Capel M, Chance M R, Gaasterland T, Lin D, Sali A, Studier F W and Swaminathan S. 1999. Structural genomics: beyond the Human Genome Project. Nature Genetics 23: 151–157.

Fassina G, Zamai M, Burke M B, Chaiken, M. 1989. Recognition properties of antisense peptides to Arg8-vasopressin/bovine neurophysin II biosynthetic precursor sequences. Biochemistry 28, 8811–8818.

Fishman M and Adler F L. 1967 Cold Spring Harbour Symp. Quant. Biol. 32: 343–350 Gaasterland T. Structural genomics: Bioinformatics in the driver's seat. Nature Biotechnology 16: 645–627, 1998.

Goldberg D. E. 1989. Genetic algorithms in search optimisation and machine learning. Addison-Wesley.

Goldstein D J. 1998. An unacknowledged problem for structural genomics? Nature Biotechnology 16: 696–697.

Kohler H and Blalock E. 1998. The hydropathic binary code: a tool in genomic research? Nature Biotechnology 16: 601.

Kyte J and Doolittle RF. 1982. A simple method for displaying the hydropathic character of a protein. J Mol Biol 5:105–132.

Mekler L B. 1969 Specific selective interaction between amino acid groups of polypeptide chains Biofizika 14: 581–584.

Mekler L B and Idlis R G. 1981 Deposited Doc. VINITI 1476–81.

Root-Bernstein R S and Holsworthy D D. 1988. Antisense peptides: a critical mini-review. J. Theor. Biol. 190: 107–119.

Root-Bernstein R S. 1982. Amino acid pairing. J Theor Biol. 94:885–94.

Sansom C. 1998. Extending the boundaries of molecular modelling. Nature Biotechnology 16: 917–918.

Shai Y, Brunck T K and Chaiken I M. 1989. Antisense peptide recognition of sense peptides: sequence simplification and evaluation of forces underlying the interaction. Biochemistry. 28: 8804–11.

Stryer L. Biochmistry. $4^{th}$ Edition. Freeman and Company, New York 1997.

Zull J E, Taylor R C, Michaels G S and Rushforth N B. 1994. Nucleic acid sequences coding for internal antisense peptides: are there implications for protein folding and evolution? Nucleic Acids Res. 22: 3373–80.

TABLE 7

EXAMPLES OF PROTEINS TO WHICH COMPLEMENTARY PEPTIDES CAN BE IDENTIFIED BY ANTISENSE LIGAND SEARCHER (ALS) IN THE SWISSPROT DATABASE
Frame Size 10: Swiss Prot DB: 50 significant proteins

| Accession No. | Description | Length | No. | No | No. RT | Total | Ex( ) |
|---|---|---|---|---|---|---|---|
| SHEEP (P50415) | BACTENECIN 7 PRECURSOR (BAC7) | 190 | 8 | 8 | 4 | 16 | 9.89E–05 |
| CHICK (Q98937) | TRANSCRIPTION FACTOR BF-2 | 440 | 22 | 26 | 0 | 48 | 0.00053 |
| HUMAN (P55316) | TRANSCRIPTION FACTOR BF-2 | 469 | 12 | 4 | 0 | 16 | 0.000603 |
| MOUSE (Q61345) | TRANSCRIPTION FACTOR BF-2 | 456 | 22 | 18 | 1 | 40 | 0.00057 |
| HUMAN (Q12837) | BRAIN-SPECIFIC HOMEOBOX | 410 | 40 | 53 | 1 | 93 | 0.000461 |
| MOUSE (Q63934) | BRAIN-SPECIFIC HOMEOBOX | 411 | 108 | 127 | 1 | 235 | 0.000463 |
| HUMAN (P20264) | BRAIN-SPECIFIC HOMEOBOX | 500 | 102 | 103 | 1 | 205 | 0.000685 |
| MOUSE (P31361) | BRAIN-SPECIFIC HOMEOBOX | 495 | 82 | 83 | 1 | 165 | 0.000671 |
| DROME (Q24266) | TRANSCRIPTION FACTOR BTD | 644 | 28 | 32 | 0 | 6 | 0.001 |
| GVCL (P41726) | DNA-BINDING PROTEIN | 58 | 48 | 54 | 10 | 102 | 9.22E–06 |
| HUMAN (P02452) | PROCOLLAGEN ALPHA 1(I) | 1464 | 6 | 62 | 4 | 68 | 0.005873 |
| HUMAN (P02458) | PROCOLLAGEN ALPHA 1(II) | 1418 | 6 | 22 | 2 | 28 | 0.005509 |

TABLE 7-continued

EXAMPLES OF PROTEINS TO WHICH COMPLEMENTARY PEPTIDES CAN BE IDENTIFIED BY ANTISENSE LIGAND SEARCHER (ALS) IN THE SWISSPROT DATABASE

Frame Size 10: Swiss Prot DB: 50 significant proteins

| Accession No. | Description | Length | No. | No | No. RT | Total | Ex( ) |
|---|---|---|---|---|---|---|---|
| MOUSE (P28481) | PROCOLLAGEN ALPHA 1(II) | 1459 | 8 | 31 | 3 | 39 | 0.005833 |
| BOVIN (P04258) | COLLAGEN ALPHA 1(III) CHAIN | 1049 | 8 | 17 | 3 | 25 | 0.003015 |
| HUMAN (P02461) | PROCOLLAGEN ALPHA 1(III) | 1466 | 8 | 28 | 2 | 36 | 0.005889 |
| BOVIN (Q28083) | COLLAGEN ALPHA 1(XI) CHAIN | 911 | 8 | 4 | 0 | 12 | 0.002274 |
| MOUSE (Q01149) | PROCOLLAGEN ALPHA 2(I | 1373 | 14 | 84 | 4 | 98 | 0.005165 |
| MOUSE (Q99020) | CARG-BINDING FACTOR-A (CBF-A) | 285 | 6 | 9 | 3 | 15 | 0.000223 |
| HUMAN (P22681) | PROTO-ONCOGENE C-CBL | 906 | 12 | 2 | 0 | 14 | 0.002249 |
| HUMAN (Q13319) | CYCLIN-DEPENDENT KINASE 5 | 367 | 6 | 1 | 0 | 7 | 0.000369 |
| DROME (P17970) | VOLTAGE-GATED POTASSIUM CH | 924 | 162 | 162 | 18 | 324 | 0.002339 |
| DROME (Q02280) | POTASSIUM CHANNEL PROTEIN E | 1174 | 38 | 63 | 9 | 101 | 0.003776 |
| RAT (Q09167) | SULIN-INDUCED GROWTH | 269 | 32 | 42 | 8 | 74 | 0.000198 |
| CHICK (Q90611) | 72 KD TYPE IV COLLAGENASE | 663 | 8 | 8 | 4 | 16 | 0.001204 |
| HPBVF (P29178) | CORE ANTIGEN | 195 | 14 | 15 | 3 | 29 | 0.000104 |
| DROME (P32027) | FORK HEAD DOMAIN PROTEIN | 508 | 50 | 40 | 0 | 90 | 0.000707 |
| CRYPA (P52753) | CRYPARIN PRECURSOR | 118 | 18 | 18 | 6 | 36 | 3.82E−05 |
| CANFA (P30803) | ADENYLATE CYCLASE, TYPE V | 1184 | 55 | 34 | 3 | 89 | 0.003841 |
| RABIT (P40144) | ADENYLATE CYCLASE, TYPE V | 1264 | 25 | 21 | 3 | 46 | 0.004378 |
| DICDI (P54639) | CYSTEINE PROTEINASE 4 PRO . . . | 442 | 84 | 82 | 14 | 166 | 0.000535 |
| ORYSA (P22913) | DEHYDRIN RAB 16D | 151 | 8 | 22 | 0 | 30 | 6.25E−05 |
| ORYSA (P12253) | WATER-STRESS INDUCIBLE PRO . . . | 163 | 14 | 12 | 4 | 26 | 7.28E−05 |
| RAPSA (P21298) | LATE EMBRYOGENESIS ABUNDANT | 184 | 24 | 20 | 0 | 44 | 9.2BE−05 |
| DROME (P23792) | DISCONNECTED PROTEIN | 568 | 27 | 28 | 8 | 55 | 0.000884 |
| DROME (Q24563) | DOPAMINE RECEPTOR 2 | 539 | 8 | 0 | 0 | 8 | 0.000796 |
| DICDI (Q04503) | PRESPORE PROTEIN DP87 PRE . . . | 555 | 22 | 17 | 1 | 39 | 0.000844 |
| DROME (P23022) | DOUBLESEX PROTEIN | 427 | 56 | 68 | 0 | 124 | 0.0005 |
| DROME (P23023) | DOUBLESEX PROTEIN, MALE-SP . . . | 549 | 70 | 88 | 0 | 158 | 0.000826 |
| DROME (Q27368) | TRANSCRIPTION FACTOR E2F | 805 | 6 | 11 | 1 | 17 | 0.001776 |
| DROME (P20105) | ECDYSONE-INDUCED PROTEIN 7 | 829 | 8 | 5 | 1 | 13 | 0.001883 |
| DROME (P11536) | ECDYSONE-INDUCED PROTEIN 7 | 883 | 80 | 83 | 1 | 163 | 0.002136 |
| EBV (P12978) | BNA-2 NUCLEAR PROTEIN | 487 | 174 | 178 | 0 | 352 | 0.00065 |
| HUMAN (P18146) | EARLY GROWTH RESPONSE PRO . . . | 543 | 12 | 17 | 1 | 29 | 0.000808 |
| MOUSE (P49749) | HOMEOBOX EVEN-SKIPPED HOM . . . | 475 | 223 | 208 | 0 | 431 | 0.000618 |
| HUMAN (Q12947) | FORKHEAD-RELATED TRANSCR . . . | 408 | 10 | 20 | 0 | 30 | 0.000456 |
| HUMAN (Q16676) | FORKHEAD-RELATED TRANSCR . . . | 465 | 14 | 7 | 1 | 21 | 0.000592 |
| DROME (P33244) | NUCLEAR HORMONE RECEPTOR | 1043 | 104 | 118 | 12 | 222 | 0.002981 |
| BURCE (P24127) | FUSARIC ACID RESISTANCE PRO . . . | 142 | 6 | 0 | 0 | 6 | 5.52E−05 |
| SCHPO (P41891) | GAR2 PROTEIN | 500 | 8 | 8 | 0 | 16 | 0.000685 |
| HUMAN (P43694) | TRANSCRIPTION FACTOR GATA-4 | 442 | 12 | 12 | 2 | 24 | 0.000535 |

We claim:

1. A method for processing sequence data comprising:
   a) selecting at least a first protein sequence and a second protein sequence;
   b) selecting a frame having a size corresponding to at least one sequence element;
   c) selecting a score threshold;
   d) selecting a frame existence probability threshold;
   e) comparing each frame of the first sequence with each frame of the second sequence by comparing pairs of sequence elements at corresponding positions within each such pair of frames to evaluate a complementary relationship score for each pair of frames;
   f) storing details of any pairs of frames for which the complementary relationship score equals or exceeds the score threshold;
   g) evaluating for each stored pair of frames the probability of that complementary pair of frames existing on the basis of the number of possible complementary sequence elements existing for each sequence element in the pair of frames;
   h) discarding any stored pairs of frames for which the evaluated probability is greater than the probability threshold; and
   i) selecting the complementary sequences thus identified.

2. The method of claim 1, wherein the sequence element is an amino acid or a triplet codon.

3. The method of claim 2, wherein the first sequence is identical to the second sequence and a frame at a given position in the first sequence is only compared with frames in the second sequence at the same given position or at a later position in the second sequence.

4. The method of claim 3, wherein the sequence elements at corresponding positions within each of a pair of frames are compared sequentially, each such pair of sequence elements generating a score that is added to an aggregate score for the pair of frames.

5. The method of claim 4, wherein if the aggregate score reaches the score threshold before all the pairs of sequence elements in the pair of frames have been compared, details of the pair of frames are immediately stored and a new pair of frames is selected for comparison.

6. The method of claim 2, wherein the sequence elements at corresponding positions within each of a pair of frames are compared sequentially, each such pair of sequence elements generating a score that is added to an aggregate score for the pair of frames.

7. The method of claim 6, wherein if the aggregate score reaches the score threshold before all the pairs of sequence elements in the pair of frames have been compared, details of the pair of frames are immediately stored and a new pair of frames is selected for comparison.

8. The method of any of claims 2–7, wherein the sequence elements are amino acids and pairs of amino acids are compared by using an antisense score list.

9. The method of claim 8, wherein the amino acid pairings are as illustrated in Table 4.

10. The method of any of claims 2–7, wherein the sequence elements are triplet codons, and pairs of codons in corresponding positions within each of the pairs of triplet codons are compared by using an antisense score list.

11. The method of claim 1, wherein the method is performed by a computer program.

12. A computer-readable medium carrying a computer program that implements the method of claim 1.

13. A computer system, comprising:
   a. memory having instructions for implementing the method of claim 1; and
   b. a processor that executes the instructions.

14. A method for processing protein sequence data to obtain an antisense scoring matrix for each possible combination of linear sequences of a given frame length, comprising:
   a) loading a first protein sequence represented by characters;
   b) loading a second protein sequence represented by characters;
   c) selecting a score threshold value x;
   d) comparing the first and second sequences to determine whether they are identical or different;
   e) when the first and second sequence are different, selecting a frame of length n amino acids for each protein sequence, wherein the position for the frame for the first sequence is determined by a setting the value of a parameter ip1 and the position for the frame for the second sequence is determined by a setting the value of a parameter ip2, wherein said frames constitute a pair of frames, or
   when the first and second sequence are identical, at all times setting the value of ip2 to at least the value of ip1;
   f) aligning each frame in the pair whereby a frame position parameter f is set to zero;
   g) comparing the first pair of amino acids in the frames by determining and multiplying the ASCII character codes for the single characters representing the amino acids in the respective frames to obtain a product;
   h) comparing the product with a list of predetermined scores representing the antisense relationships shown in Tables 2 and 4, wherein if the product matches one of the predetermined scores, than an output value T is set to 1, or if the product does not match one of the predetermined scores, then the output parameter T is set to zero;

i) adding the output value to an aggregate score iS;
j) determining whether the aggregate score iS is greater than the score threshold value x, wherein;
if iS is greater than x, then a result for the pair of frames is stored for further analysis; or
if iS is equal to or less than x, determining whether it is possible for the pair of frames to yield the score threshold x, wherein if it is possible the frame processing continues and f is incremented such that the next pair of amino acids is compared or if the pair of frames cannot yield the score threshold x, a next frame is selected;
k) repeating e) through j) until ip2 is equal to the length of the second sequence, wherein each time e) through j) are completed the value of ip1 is zeroed and then incremented until all frames of sequence one have been analyzed against all frames of the second sequence;
l) reversing sequence 1;
m) repeating steps e) through k) to obtain an antisense scoring matrix for each possible combination of linear sequences at a given frame length; and
n) selecting a complementary sequence from the antisense scoring matrix thus obtained.

15. The method of claim 14, further comprising:
a) selecting a result for the pair of frames stored for further analysis in j) of claim 14, said result comprising information on frame location, frame length, a sum of scores for the frame, and a frame type, wherein the frame type is forward or reverse depending on the orientation of the first and second protein sequences with respect to one another;
b) selecting a probability value p;
c) using the information in a) to calculate the probability of the pair of frames existing; and
d) comparing the probability from c) to the probablility from b), wherein if the calculated probability is less than the probability value p, then the frame information is stored for inclusion in a final result set.

16. A method for processing nucleotide sequence data to obtain an antisense scoring matrix for each possible combination of linear sequences of a given frame length, comprising:
a) loading a first nucleic acid sequence represented by characters;
b) loading a second nucleic acid sequence represented by characters;
c) selecting a score threshold value x;
d) comparing the first and second sequences to determine whether they are identical or different;
e) selecting a frame having a length of 3 nucleotides for each nucleic acid sequence, wherein the position for the frame for the first sequence is determined by a setting the value of a parameter ip1 and the position for the frame for the second sequence is determined by a setting the value of a parameter ip2, wherein said frames constitute a pair of frames, or
when the first and second sequence are identical, at all times setting the value of ip2 to at least the value of ip1;
f) aligning each frame in the pair whereby a frame position parameter f is set to zero;
g) comparing the second pair of nucleotides in each of the frames by determining and multiplying the ASCII character codes for the characters representing the nucleotides in the respective frames to obtain a product, wherein said product is compared to a list as shown in Table 4 to determine if the nucleotides are complementary;
h) when the second pair of nucleotides are complementary, repeating g) for the first and third pairs of nucleotides in the pair of frames, wherein if any pair of nucleotides in the pair of frames is not complementary, than an output parameter T is set to a value of zero, or if all of the nucleotide pairs in the pair of frames are complementary, then the output parameter T is set to a value of 1;
i) adding the output value to an aggregate score iS;
j) determining whether the aggregate score iS is greater than the score threshold value x, wherein;
if iS is greater than x, then the pair of frames is stored for further analysis; or if iS is equal to or less than x, determining whether it is possible for the pair of frames to yield the score threshold x, wherein if it is possible the frame processing continues and f is incremented such that the next pair of amino acids is compared or if the pair of frames cannot yield the score threshold x, a next frame is selected;
k) repeating e) through j) until ip2 is equal to the length of the second sequence, wherein each time e) through j) are completed the value of ip1 is zeroed and then incremented until all frames of sequence one have been analyzed against all frames of the second sequence;
l) reversing sequence 1;
m) repeating steps e) through k) to obtain an antisense scoring matrix for each possible combination of linear sequences at a given frame length; and
n) selecting a complementary sequence from the antisense scoring matrix thus obtained.

* * * * *